United States Patent
Wang et al.

(10) Patent No.: US 10,357,218 B2
(45) Date of Patent: Jul. 23, 2019

(54) METHODS AND SYSTEMS FOR EXTRACTING BLOOD VESSEL

(71) Applicant: SHANGHAI UNITED IMAGING HEALTHCARE CO., LTD., Shanghai (CN)

(72) Inventors: Xiaodong Wang, Shanghai (CN); Wenjun Yu, Shanghai (CN); Yufei Mao, Shanghai (CN); Xu Wang, Shanghai (CN); Ke Wu, Shanghai (CN); Ce Wang, Shanghai (CN); Peng Zhao, Shanghai (CN); Chuanfeng Lv, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 3 days.

(21) Appl. No.: 15/663,909

(22) Filed: Jul. 31, 2017

(65) Prior Publication Data
US 2018/0000441 A1    Jan. 4, 2018

Related U.S. Application Data

(63) Continuation of application No. PCT/CN2017/088276, filed on Jun. 14, 2017.

(30) Foreign Application Priority Data

Jun. 30, 2016  (CN) .......................... 2016 1 0503562
Jul. 29, 2016  (CN) .......................... 2016 1 0608532
(Continued)

(51) Int. Cl.
G06K 9/62    (2006.01)
A61B 6/00    (2006.01)
(Continued)

(52) U.S. Cl.
CPC ............ *A61B 6/5294* (2013.01); *A61B 5/004* (2013.01); *A61B 5/0037* (2013.01); *A61B 5/489* (2013.01);
(Continued)

(58) Field of Classification Search
CPC ........................................... G06T 2207/30172
See application file for complete search history.

(56) References Cited

U.S. PATENT DOCUMENTS 7,177,453 B2    2/2007    Suryanarayanan et al.
7,602,970 B2   10/2009    Florin et al.
(Continued)

FOREIGN PATENT DOCUMENTS

CN    1430185 A    7/2003
CN    1700254 A   11/2005
(Continued)

OTHER PUBLICATIONS

Cuisenaire, O, Fully automated segmentation of carotid and vertebral arteries from CTA, SPIE Medical Imaging, 6914(69143R): 1-10 (2009).
(Continued)

*Primary Examiner* — Gandhi Thirugnanam
(74) *Attorney, Agent, or Firm* — Metis IP LLC

(57) ABSTRACT

A method for extracting a blood vessel is provided. An image relating to a blood vessel may be acquired. The image may include multiple slices. A region of interest in the image may be determined. A blood vessel model may be obtained. The blood vessel may be extracted from the region of interest based on the blood vessel model.

15 Claims, 21 Drawing Sheets

(30) Foreign Application Priority Data

| Jul. 29, 2016 | (CN) | 2016 1 0609053 |
|---|---|---|
| Aug. 18, 2016 | (CN) | 2016 1 0686885 |
| Dec. 15, 2016 | (CN) | 2016 1 1163876 |
| Apr. 28, 2017 | (CN) | 2017 1 0297072 |
| May 3, 2017 | (CN) | 2017 1 0303879 |

(51) Int. Cl.

| G06T 7/136 | (2017.01) |
|---|---|
| G06T 7/11 | (2017.01) |
| G06K 9/20 | (2006.01) |
| G06K 9/46 | (2006.01) |
| G06T 5/30 | (2006.01) |
| G06T 7/00 | (2017.01) |
| A61B 5/00 | (2006.01) |
| A61B 5/055 | (2006.01) |
| A61B 6/03 | (2006.01) |

(52) U.S. Cl.
CPC ............ *G06K 9/2054* (2013.01); *G06K 9/46* (2013.01); *G06K 9/6256* (2013.01); *G06K 9/6267* (2013.01); *G06T 5/30* (2013.01); *G06T 7/0014* (2013.01); *G06T 7/11* (2017.01); *G06T 7/136* (2017.01); *A61B 5/055* (2013.01); *A61B 6/037* (2013.01); *A61B 6/504* (2013.01); *G06T 2200/04* (2013.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/20021* (2013.01); *G06T 2207/20081* (2013.01); *G06T 2207/30101* (2013.01); *G06T 2207/30172* (2013.01)

(56) References Cited

U.S. PATENT DOCUMENTS

| 7,953,266 | B2 | 5/2011 | Gulsun et al. | |
|---|---|---|---|---|
| 8,126,232 | B2 | 2/2012 | Dikici et al. | |
| 8,135,195 | B2 | 3/2012 | Mahesh et al. | |
| 9,805,463 | B2* | 10/2017 | Choi | A61B 5/02007 |
| 2005/0148877 | A1* | 7/2005 | Guo | A61B 8/14 600/459 |
| 2006/0251325 | A1* | 11/2006 | Florin | G06T 7/12 382/173 |
| 2006/0280351 | A1* | 12/2006 | Luping | G06K 9/00201 382/128 |
| 2007/0081706 | A1* | 4/2007 | Zhou | G06F 19/321 382/128 |
| 2007/0165952 | A1 | 7/2007 | Goto | |
| 2007/0260135 | A1* | 11/2007 | Rousson | G06K 9/34 600/407 |
| 2008/0094389 | A1 | 4/2008 | Rouet et al. | |
| 2010/0014740 | A1 | 1/2010 | Movassaghi et al. | |
| 2010/0074493 | A1* | 3/2010 | Wiemker | A61B 6/032 382/130 |
| 2010/0296718 | A1 | 11/2010 | Ostrovsky-Berman et al. | |
| 2012/0201442 | A1 | 8/2012 | Beck et al. | |
| 2012/0207366 | A1 | 8/2012 | Liu | |
| 2013/0064435 | A1* | 3/2013 | Taerum | G06K 9/6207 382/128 |
| 2016/0133015 | A1* | 5/2016 | Taylor | A61B 5/02007 382/128 |
| 2017/0311916 | A1 | 11/2017 | Yagi et al. | |
| 2018/0000441 | A1* | 1/2018 | Wang | G06T 7/136 |

FOREIGN PATENT DOCUMENTS

| CN | 1779718 A | 5/2006 |
|---|---|---|
| CN | 101013503 A | 8/2007 |
| CN | 101425186 A | 5/2009 |
| CN | 101551906 A | 10/2009 |
| CN | 101706843 A | 5/2010 |
| CN | 101393644 B | 8/2010 |
| CN | 101996329 A | 3/2011 |
| CN | 102332054 A | 1/2012 |
| CN | 102402796 A | 4/2012 |
| CN | 102930552 A | 2/2013 |
| CN | 103164859 A | 6/2013 |
| CN | 103247073 A | 8/2013 |
| CN | 103279741 A | 9/2013 |
| CN | 103284760 A | 9/2013 |
| CN | 103295200 A | 9/2013 |
| CN | 103593829 A | 2/2014 |
| CN | 103679801 A | 3/2014 |
| CN | 103810363 A | 5/2014 |
| CN | 103810709 A | 5/2014 |
| CN | 103871036 A | 6/2014 |
| CN | 103985123 A | 8/2014 |
| CN | 104091346 A | 10/2014 |
| CN | 104166979 A | 11/2014 |
| CN | 104240220 A | 12/2014 |
| CN | 104463830 A | 3/2015 |
| CN | 104463860 A | 3/2015 |
| CN | 104766293 A | 7/2015 |
| CN | 104809480 A | 7/2015 |
| CN | 105069803 A | 11/2015 |
| CN | 105118056 A | 12/2015 |
| CN | 105427277 A | 3/2016 |
| CN | 105741251 A | 7/2016 |
| CN | 106157320 A | 11/2016 |
| CN | 106228561 A | 12/2016 |
| EP | 1901232 B1 | 3/2011 |
| EP | 2357609 B1 | 6/2012 |

OTHER PUBLICATIONS

Freiman, M et al., Nearly automatic vessels segmentation using graph-based energy minimization, The Midas Journal, (2009).

Shim, H et al., Partition-Based Extraction of Cerebral Arteries from CT Angiography with Emphasis on Adaptive Tracking, G.E. Christensen and M. Sonka (Eds.): IPMI 2005, LNCS 3565, 357-368 (2005).

Vieco, P T et al., Detection of circle of Willis Aneurysms in Patients with Acute Subarachnoid Hemorrhage: A Comparison of CT Angiography and Digital Subtraction Angiography, AJR, 165(2): 425-430 (1995).

Lyu, F J et al., Atlas of Clinical Application of VCTDSA in Cerebral Vessels, People's Military Medical Press, May 2010, pp. 2-6, 11-13.

Kirbas, C et al., A review of vessel extraction techniques and algorithms, ACM Computing Surveys, 36(2): 81-121 (2004).

Wink, O et al., Fast Delineation and Visualization of Vessels in 3-D Angiographic Images, IEEE Transactions on Medical Imading, 19(4): 337-346 (2000).

Wink, O et al., Multiscale Vessel Tracking, IEEE Transactions on Medical Imading, 23(1): 130-133 (2004).

Manniesing R et al., Vessel Axis Tracking Using Topology Constrained Surface Evolution. IEEE Transactions on Medical Imading, 26(3): 309-316 (2007).

Cuisenaire, O et al., Fully automated segmentation of carotid and vertebral arteries from contrast enhanced CTA, SPIE Medical Imaging, 6914(69143R): 1-8 (2008).

Shang, Q Y et al., Adaptive Directional Region Growing Segmentation of the Hepatic Vasculature, SPIE Medical Imaging, 6914(69141F): 1-10 (2008).

Tan, Y Q et al., Segmentation of lung lesions on CT scans using watershed, active contours, and Markov random field, Medical Physics, 40(4): 043502-1 to 043502-10 (2013).

Selle, D et al., Analysis of Vasculature for Liver Surgical Planning, IEEE Transactions on Medical Imaging, 21(11): 1344-1357(2002).

Kawajiri, S et al., Automated segmentation of hepatic vessels in non-contrast X-ray CT images, Radiological Physics and Technology, 1(2): 214-222 (2007).

Esneault, S et al., Liver Vessels Segmentation Using a Hybrid Geometrical Moments/Graph Cuts Method, IEEE Transactions on Biomedical Engineering, 57(2): 276-283 (2010).

(56) References Cited

OTHER PUBLICATIONS

Kaftan J N et al., A Two-Stage Approach for Fully Automatic Segmentation of Venous Vascular structures in Liver CT Images, SPIE Medical Imaging, 7259(725911): 1-12 (2009).
Manniesing R et al., Level set based cerebral vasculature segmentation and diameter quantification in CT angiography, Medical Imaging Analysis, 10(2): 200-214 (2006).
Bruijne M D et al., Adapting Active Shape Models for 3D Segmentation of Tubular Structures in Medical Images.
Bruijne M D et al., Interactive segmentation of abdominal aortic aneurysms in CTA images, Medical Imaging Analysis, 8(2): 127-138 (2004).
Schaap M et al., Bayesian Tracking of Tubular Structures and Its Application to Carotid Arteries in CTA, Med Image Comput Comput Assist Interv, 10(2): 562-570 (2007).
Passat N et al., Watershed and multimodal data for brain vessel segmentation: Application to the superior sagittal sinus, Image and Vision Computing, 25: 512-521 (2007).
Passat N et al., Region-Growing Segmentation of Brain Vessels: An Atlas-Based Automatic Approach, Journal of Magnetic Resonance Imaging, 21: 715-725 (2005).
Lupascu, C A et al., FABC: Retinal Vessel Segmentation Using AdaBoost, IEEE Transactions on Information Technology in Biomedicine, 14(5): 1267-1274 (2010).
Zhou, Lin et al., Segmentation of Retinal Blood Vessels Based on Centerline Extraction, Journal of Biomedical Engineering, 29(1): 1-6 (2012).
First Office Action for Chinese Application No. 201610686885.4 dated Aug. 3, 2018, 21 pages.
First Office Action for Chinese Application No. 201611163876.3 dated May 28, 2019, 13 pages.

\* cited by examiner

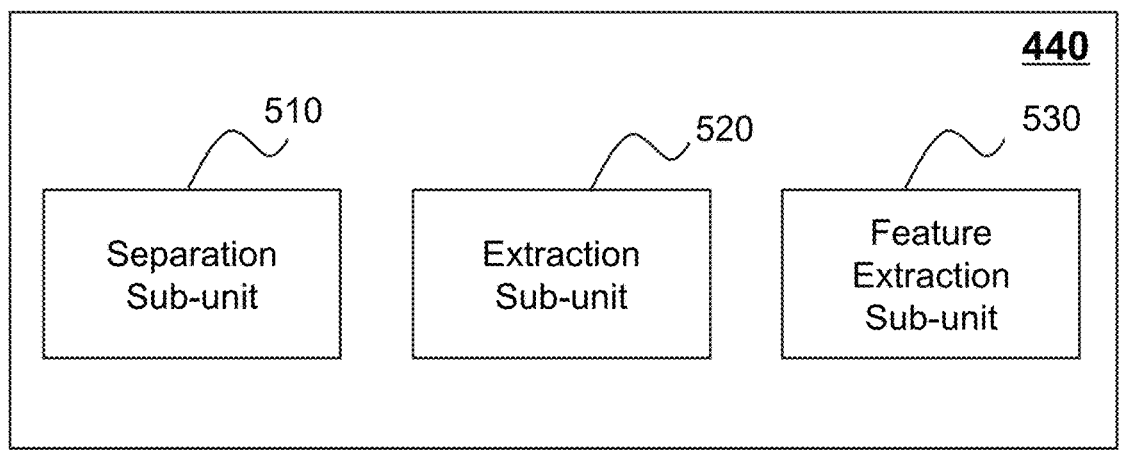
FIG. 5-A

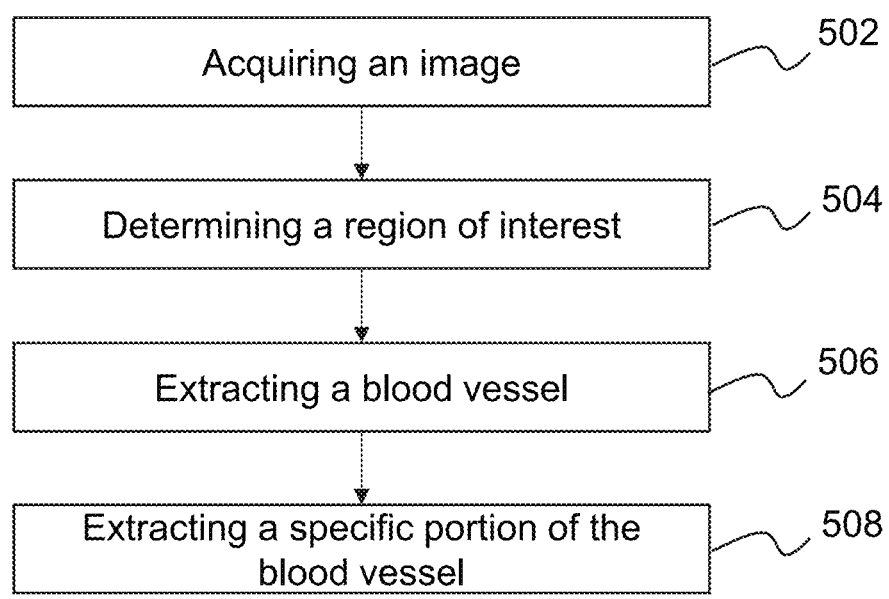
FIG. 5-B

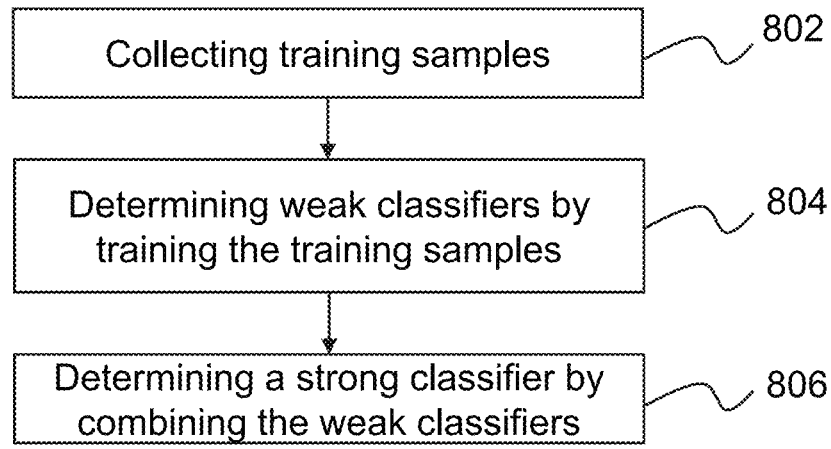
FIG. 8-A
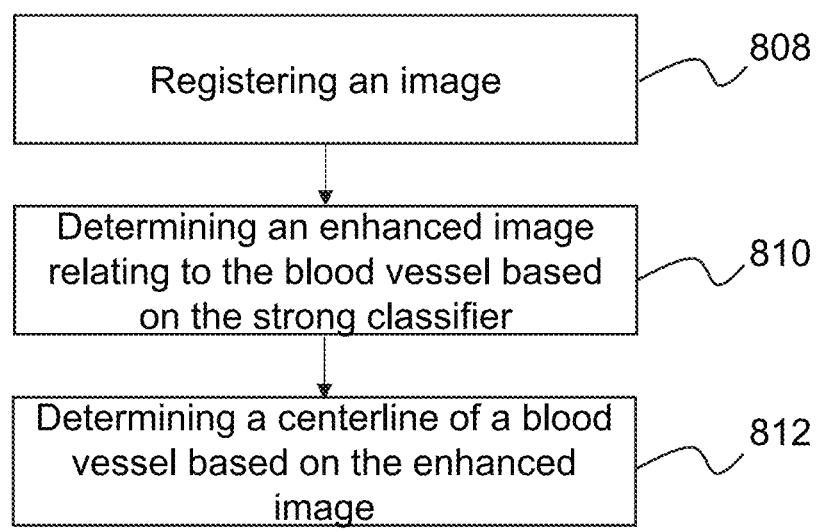
FIG. 8-B

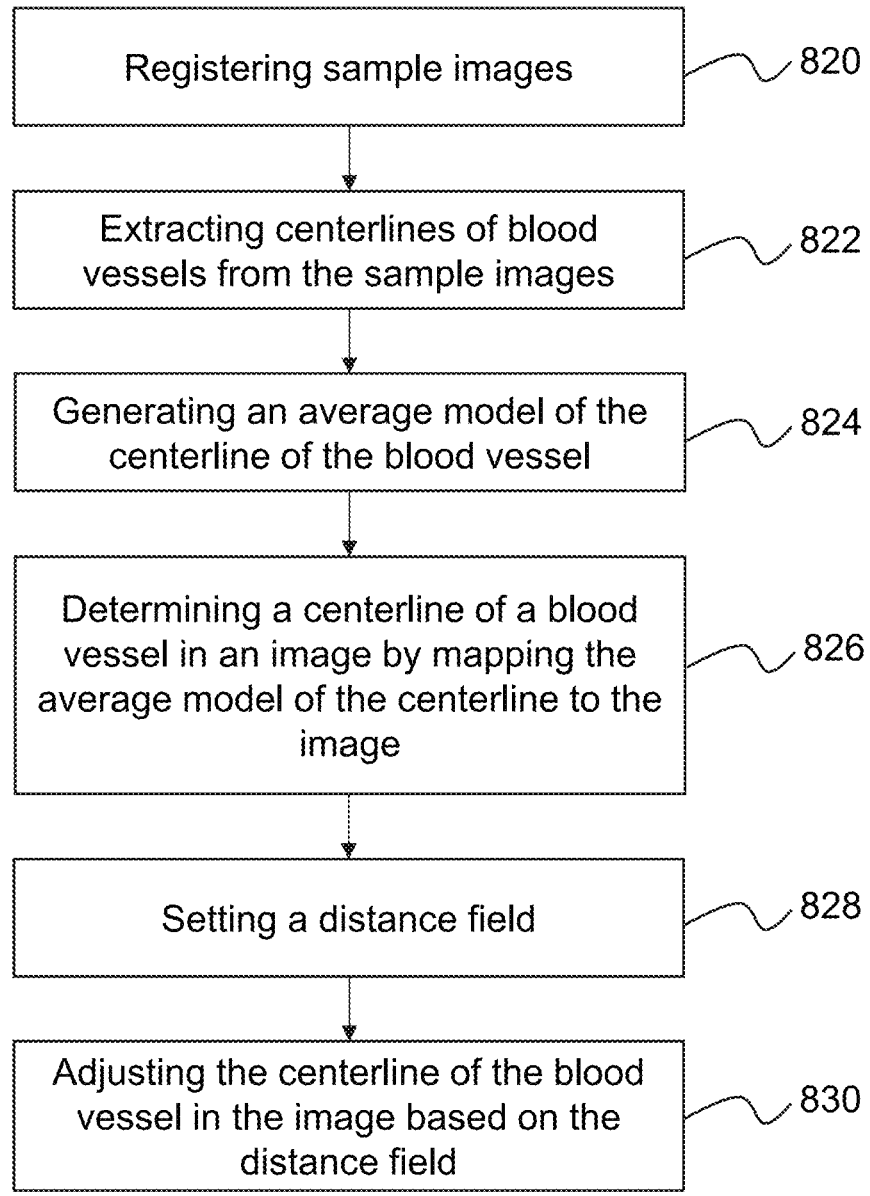
FIG. 8-C

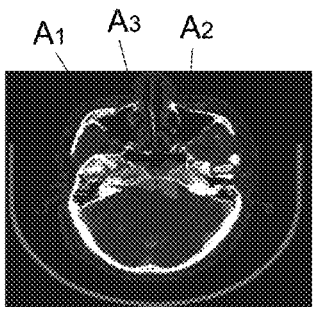
FIG. 13-A
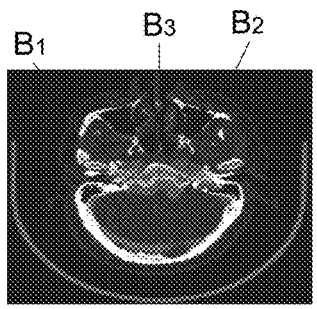
FIG. 13-B
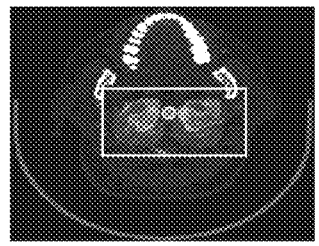
FIG. 13-C
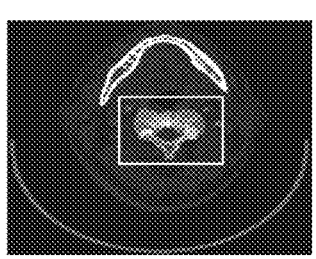
FIG. 13-D
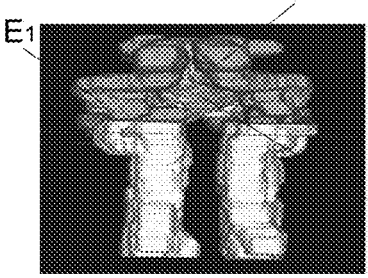
FIG. 13-E
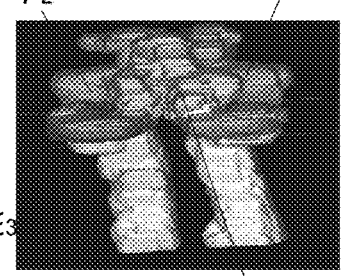
FIG. 13-F
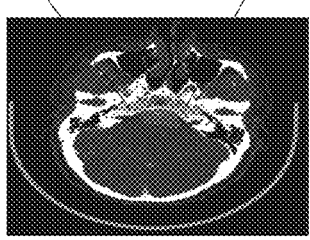
FIG. 13-G
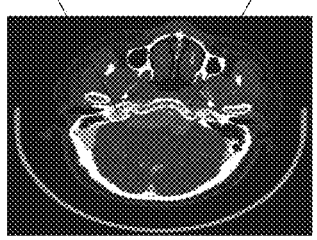
FIG. 13-H
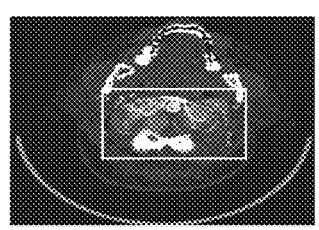
FIG. 13-I
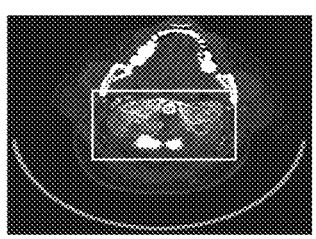
FIG. 13-J
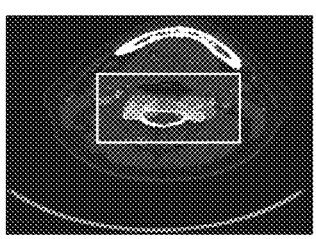
FIG. 13-K
FIG. 13-L
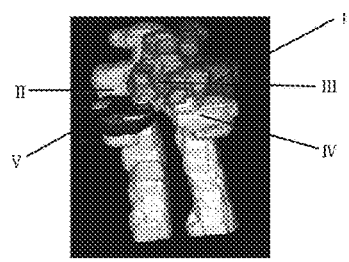
FIG. 13-M

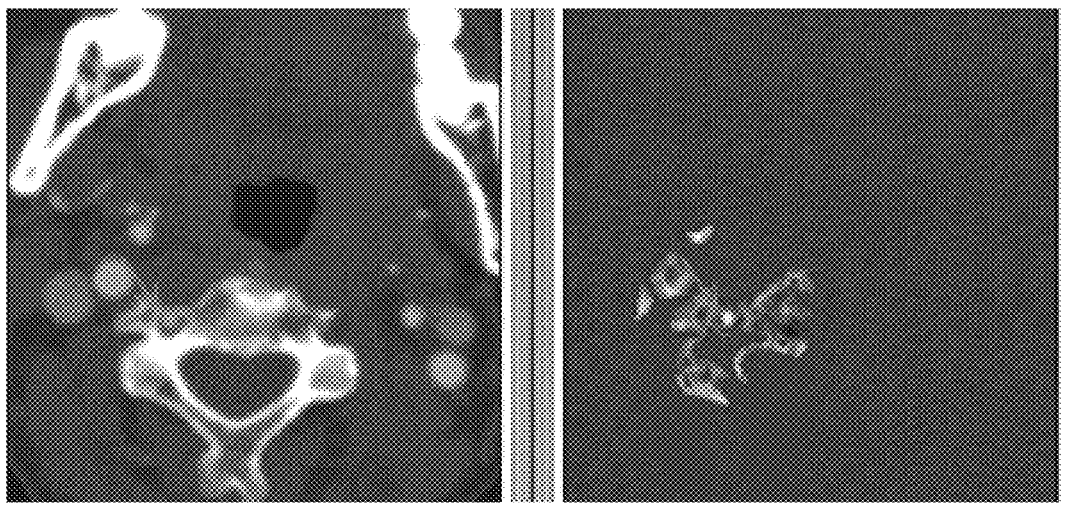
FIG. 14-A
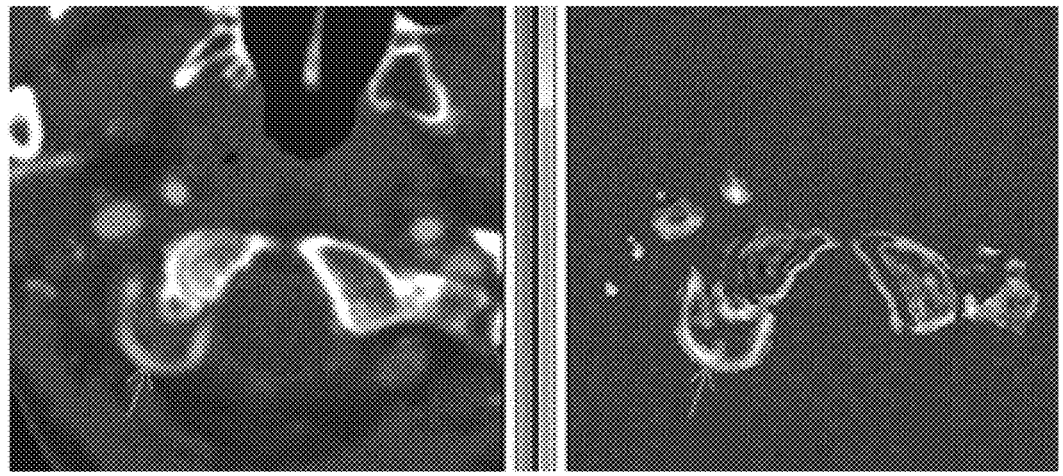
FIG. 14-B

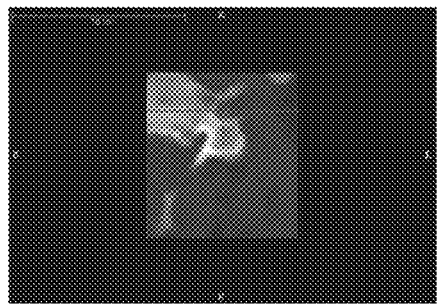
FIG. 15-A
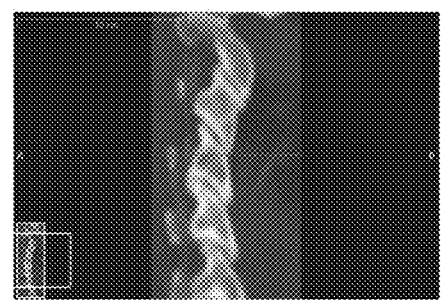
FIG. 15-B
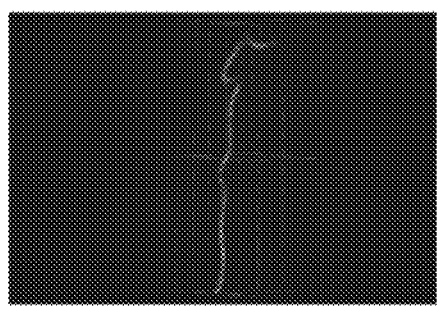
FIG. 15-C
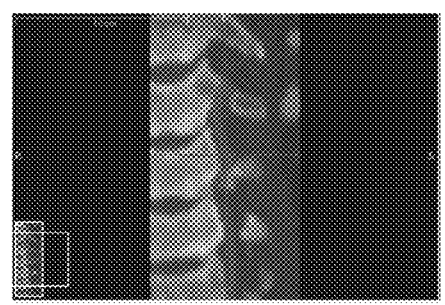
FIG. 15-D
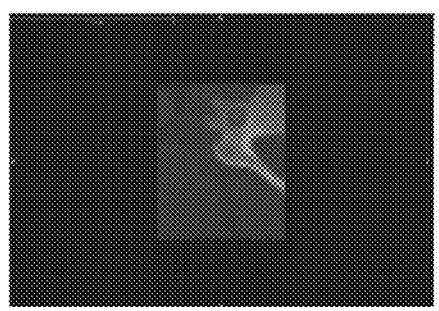
FIG. 15-E
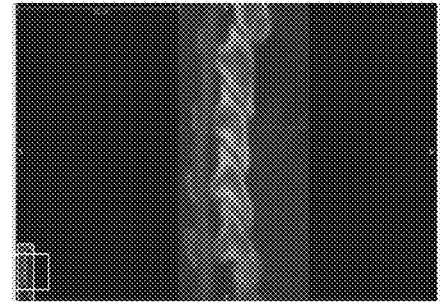
FIG. 15-F
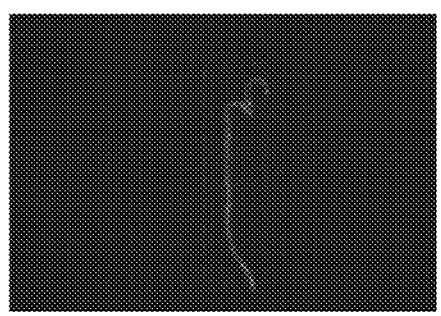
FIG. 15-G
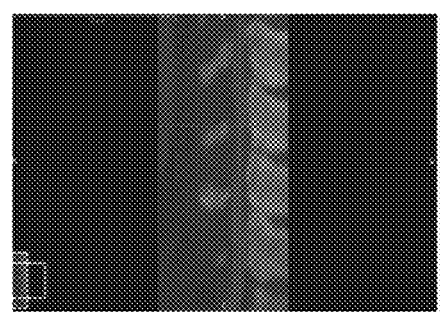
FIG. 15-H

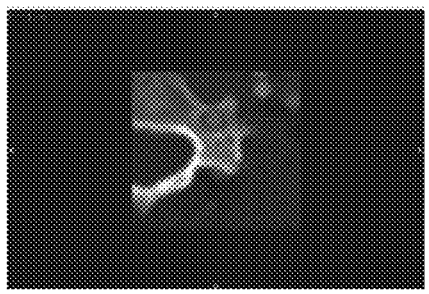
FIG. 15-I
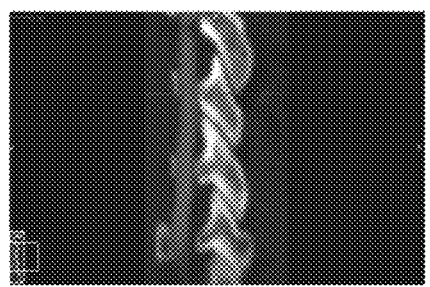
FIG. 15-J
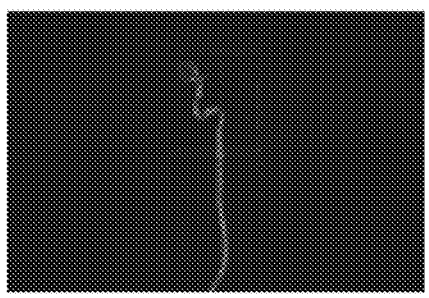
FIG. 15-K
FIG. 15-L
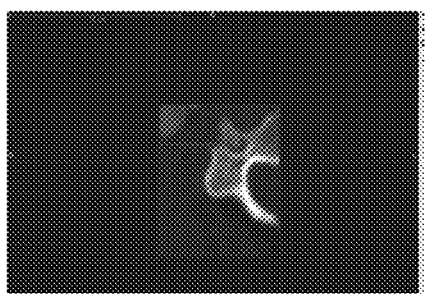
FIG. 15-M
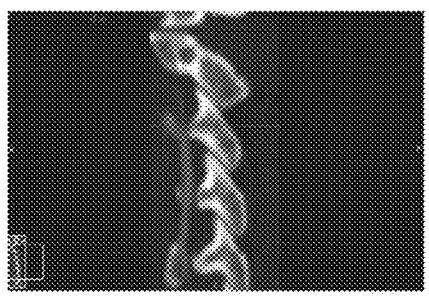
FIG. 15-N
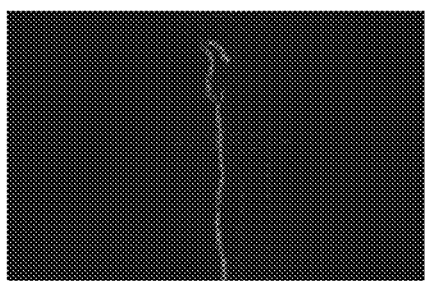
FIG. 15-O
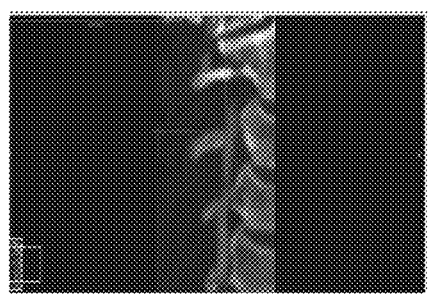
FIG. 15-P

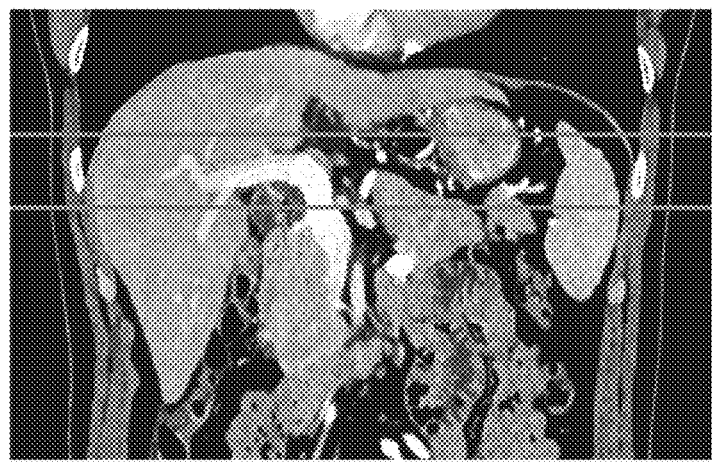
FIG. 16-A
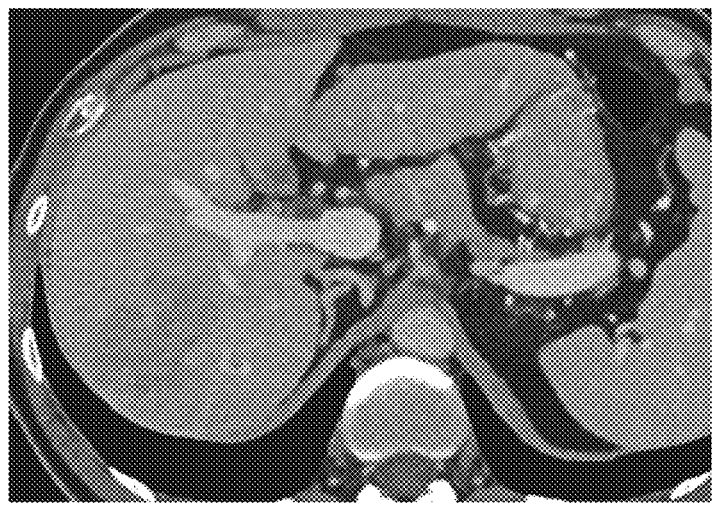
FIG. 16-B
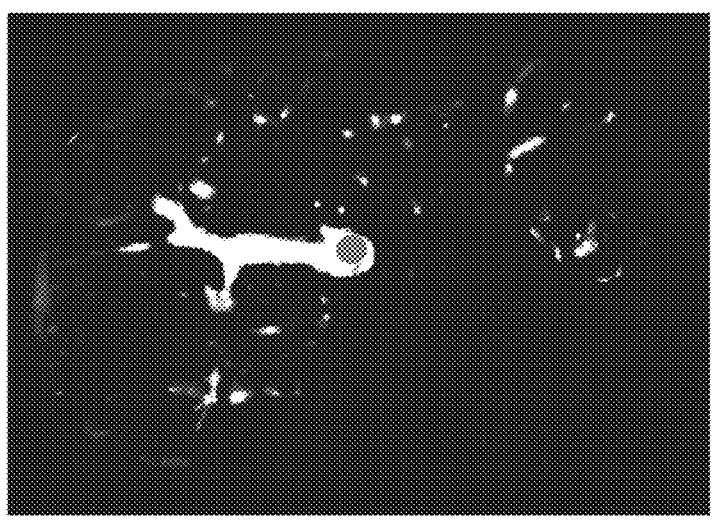
FIG. 16-C

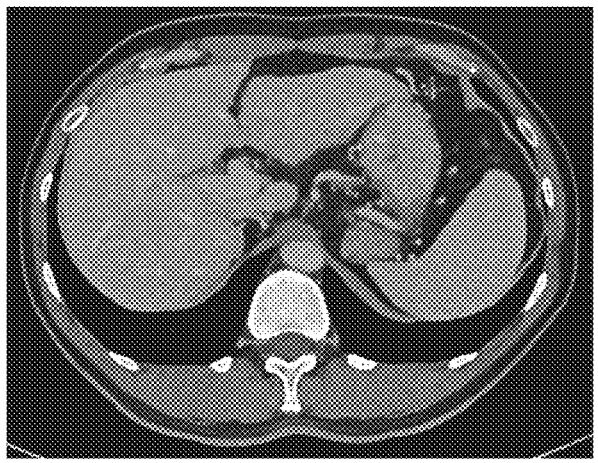
FIG. 16-D
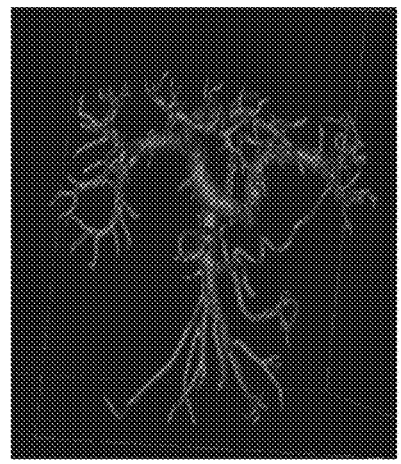
FIG. 16-E
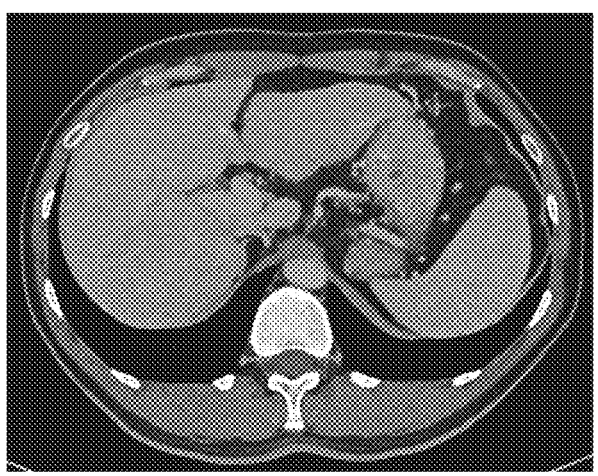
FIG. 16-F
FIG. 16-G

METHODS AND SYSTEMS FOR EXTRACTING BLOOD VESSEL

CROSS-REFERENCE TO RELATED APPLICATIONS

This application is a U.S. national stage under 35 U.S.C. § 371 of International Application No. PCT/CN2017/088276, filed on Jun. 14, 2017, designating the United States of America, which claims priority of the following applications: Chinese Application No. 201610503562.7 filed on Jun. 30, 2016, Chinese Application No. 201610608532.2 filed on Jul. 29, 2016, Chinese Application No. 201610609053.2 filed on Jul. 29, 2016, Chinese Application No. 201610686885.4 filed on Aug. 18, 2016, Chinese Application No. 201611163876.3 filed on Dec. 15, 2016, Chinese Application No. 201710297072.0 filed on Apr. 28, 2017, and Chinese Application No. 201710303879.0 filed on May 3, 2017, the entire contents of each of which are hereby incorporated by reference.

TECHNICAL FIELD

The present application relates to a medical imaging system, and more particular to methods and systems for extracting a blood vessel in a medical image.

BACKGROUND

A blood vessel imaging technology may include a CT/MR angiography, a MR non-contrast imaging, etc. The blood vessel imaging technology may be an important technology for assisting a doctor to diagnose various vascular diseases, such as calcification, stenosis, aneurysms, etc. Blood vessel images obtained in a blood vessel imaging process may be mainly three-dimensional images which cannot provide an intuitive presentation on the doctor. Therefore, it is important for diagnosing vascular diseases to extract a blood vessel from an image and show the morphology of the blood vessel with a three-dimensional display technique.

SUMMARY

According to an aspect of the present disclosure, a method for extracting a blood vessel is provided. The method may be implemented on at least one machine each of which has at least one processor and storage. The method may include acquiring an image relating to a blood vessel, the image including multiple slices; determining a region of interest in the image; establishing a blood vessel model; and extracting the blood vessel from the region of interest based on the blood vessel model.

In some embodiments, the determining a region of interest in the image may include identifying slice information relating to the multiple slices of the image; determining a slice range of the multiple slices corresponding to a sub-image based on the slice information; determining the sub-image in the slice range; acquiring a template based on the sub-image; registering the sub-image based on the template to determine a registered result; and identifying the region of interest based on the registered result.

In some embodiments, the determining a region of interest in the image may include performing machine learning.

In some embodiments, the method may further include determining a seed point of the blood vessel.

In some embodiments, the determining a seed point of the blood vessel may include performing an enhancement operation on the image to obtain an enhanced image; determining gradients of grey values relating to the image to obtain a gradient image; constructing a feature function of the blood vessel based on the enhanced image and the gradient image; and determining the seed point of the blood vessel based on the feature function of the blood vessel.

In some embodiments, the method may further include determining a centerline of the blood vessel.

In some embodiments, the determining a centerline of the blood vessel may include retrieving training samples; performing a classifier training based on the training samples to determine weak classifiers; combining the weak classifiers to determine a strong classifier; determining the enhanced image based on the strong classifier; and determining the centerline of the blood vessel in the enhanced image based on a fast marching algorithm.

In some embodiments, the training samples may include a positive training sample and a negative training sample In some embodiments, the determining a centerline of the blood vessel may include registering sample images; extracting a reference centerline of the blood vessel from the registered sample images; determining a model of the centerline of the blood vessel based on the reference centerline of the blood vessel; mapping the model of the centerline of the blood vessel to the image to determine a first centerline of the blood vessel in the image; determining a distance field in the image; and adjusting the first centerline of the blood vessel based on the distance field to determine the centerline of the blood vessel.

In some embodiments, the method may further include extracting the blood vessel based on the centerline of the blood vessel. The extracting the blood vessel based on the centerline of the blood vessel may include determining a first segmentation result based on the centerline of the blood vessel; determining a second segmentation result based on the first segmentation result; assessing the second segmentation result based on a global condition to determine a third segmentation result; determining a boundary condition relating to the blood vessel model; assessing the third segmentation result based on the boundary condition to determine a fourth segmentation result; and extracting the blood vessel based on the fourth segmentation result.

In some embodiments, the method may further include determining that the blood vessel is extracted in the region of interest; and extracting, in response to that the blood vessel is not extracted, the blood vessel based on a first method.

In some embodiments, the first method may include a segmentation technique relating to an aneurysmal blood vessel, a segmentation technique relating to a blood vessel with a low dose contrast agent, or a segmentation technique relating to a calcific malformation blood vessel.

In some embodiments, the extracting the blood vessel may include performing a statistical analysis on gray values within the region of interest; determining a growing parameter based on the statistical analysis; determining a trunk of the blood vessel based on a fast marching algorithm; and tracking a branch of the blood vessel by adjusting the growing parameter.

In some embodiments, the method may further include extracting a specific portion of the blood vessel. The extracting a specific portion of the blood vessel may include determining a region including the specific portion of the blood vessel; determining a first connected component in the region; extracting a feature of the first connected component; determining a connected component of the specific portion based on the feature of the first connected component; and determining the specific portion of the blood vessel based on the connected component of the specific portion.

In some embodiments, the feature of the first connected component may include a position, a size, or a shape of the first connected component.

In some embodiments, the determining the specific portion of the blood vessel may include performing a dilation operation or a region growing operation on the determined connected component of the specific portion.

According to an aspect of the present disclosure, a system for extracting a blood vessel is provided. The system may include at least one processor and executable instructions. When the executable instructions are executed by the at least one processor, the instructions may cause the at least one processor to implement a method. The method may include acquiring an image relating to a blood vessel, the image including multiple slices; determining a region of interest in the image; establishing a blood vessel model; and extracting the blood vessel from the region of interest based on the blood vessel model.

In some embodiments, the determining a region of interest in the image may include identifying slice information relating to the multiple slices of the image; determining a slice range of the multiple slices corresponding to a sub-image based on the slice information; determining the sub-image in the slice range; acquiring a template based on the sub-image; registering the sub-image based on the template to determine a registered result; and identifying the region of interest based on the registered result.

In some embodiments, the method may further include determining a seed point of the blood vessel including performing an enhancement operation on the image to obtain an enhanced image; determining gradients of grey values relating to the image to obtain a gradient image; constructing a feature function of the blood vessel based on the enhanced image and the gradient image; and determining the seed point of the blood vessel based on the feature function of the blood vessel.

In some embodiments, the method further include determining a centerline of the blood vessel.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include acquiring an image relating to a blood vessel, the image including multiple slices; determining a region of interest in the image; establishing a blood vessel model; and extracting the blood vessel from the region of interest based on the blood vessel model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5-A is a block diagram illustrating an exemplary blood vessel extraction unit according to some embodiments of the present disclosure;

FIG. 5-B is a flowchart illustrating an exemplary process for extracting a blood vessel according to some embodiments of the present disclosure;

FIG. 8-A is a flowchart illustrating an exemplary process for determining a strong classifier obtained based on a training according to some embodiments of the present disclosure;

FIG. 8-B is a flowchart illustrating an exemplary process for determining a centerline of a blood vessel according to some embodiments of the present disclosure;

FIG. 8-C is a flowchart illustrating an exemplary process for determining a centerline of a blood vessel according to some embodiments of the present disclosure;

FIGS. 13-A through 13-M illustrate a group of exemplary experimental result images for determining a region of interest (ROI) relating to a target blood vessel in a head-neck area according to some embodiments of the present disclosure;

FIGS. 14-A and 14-B illustrate exemplary experimental result images for determining a centerline of a blood vessel based on a training according to some embodiments of the present application;

FIGS. 15-A through 15-P illustrate a group of exemplary experimental result images for extracting a blood vessel based on a centerline of the blood vessel according to some embodiments of the present disclosure;

FIGS. 16-A through 16-G illustrate exemplary experimental result images for extracting a hepatic portal vein according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

Although this disclosure makes a variety of references to certain modules in the system according to some embodiments of the present disclosure, however, any number of different modules are used and run on the client and/or server. The modules are illustrative only, and different aspects of systems and methods may use different modules.

In the present disclosure, flowcharts is used to illustrate the operations performed by the system according to some embodiments of the present disclosure. It should be understood that the preceding or following operations are not necessarily performed accurately in sequence. On the contrary, various operations may be also performed in reverse or simultaneously. Other operations may be added to these processes, or removed from these processes.

Figure 1:
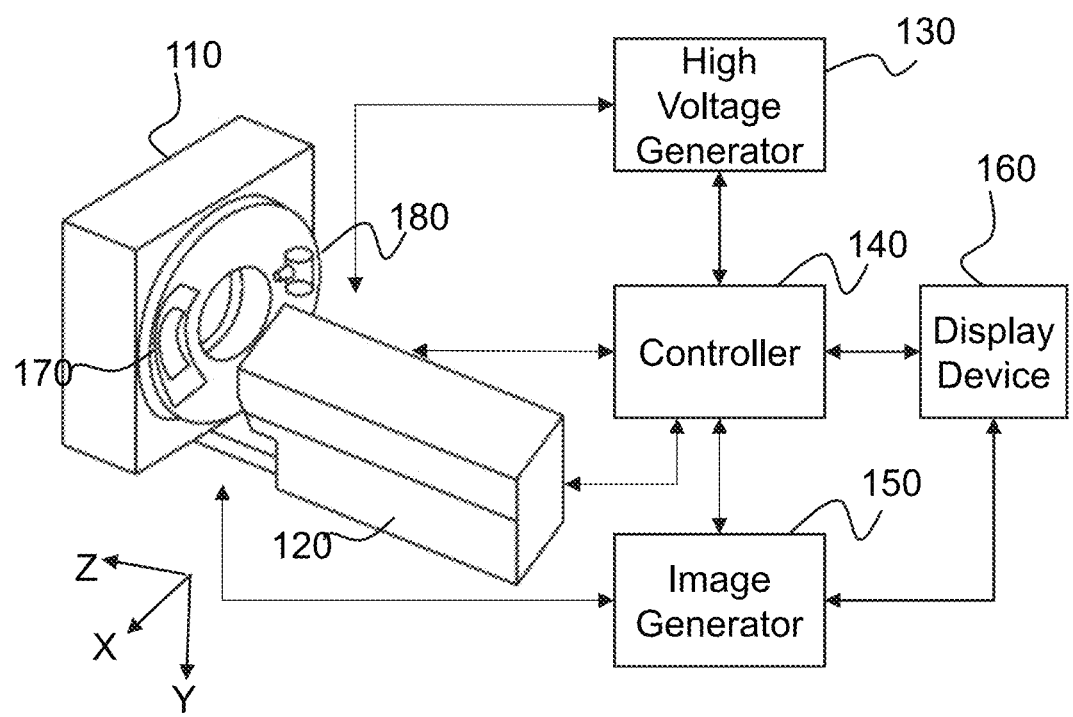
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. In some embodiments, the imaging system 100 may scan a target, obtain scan data, and generate an image relating to the target. In some embodiments, the imaging system 100 may further process the generated image. In some embodiments, the imaging system 100 may be a device or a device group. Specifically, the imaging system 100 may be a medical imaging system, for example, a positron emission tomography (PET) device, a single-photon-emission computed tomography (SPECT), a computed tomography (CT) device, a magnetic resonance imaging (MRI) device, etc. Further, the medical imaging system may include a multi-modality imaging system, for example, a PET-CT device, a PET-MRI device, a SPECT-MRI device, etc.

In some embodiments, the imaging system 100 may include a scanner. The scanner may scan a target and obtain information (e.g., scan data) relating to the target. Further, the imaging system 100 may include a radioactive scanner. The radioactive scanner may include a radioactive scanning source. The radioactive scanning source may emit a radioactive ray to a target. The radioactive ray may include a corpuscular ray, a photon ray, or the like, or a combination thereof. The corpuscular ray may include a neutron, a proton, an electron, a μ medium, a heavy ion, or the like, or a combination thereof. The photon ray may include an X-ray, a gamma ray (γ-ray), an alpha ray (α-ray), a beta ray (β-ray), an ultraviolet ray, a laser, or the like, or a combination thereof. For example, the photon ray may be the X-ray, and the corresponding imaging system may be a CT system, a digital ray (DR) imaging system, a multi-modality medical imaging system, etc. In some embodiments, the multi-modality medical imaging system may include a CT-PET system, a SPECT-MRI system, etc.

In some embodiments, the imaging system 100 may include a cavity 110, a table 120, a high voltage generator 130, a controller 140, an image generator 150, and a display device 160. In some embodiments, the cavity 110 may house a component used for generating and detecting radioactive rays. In some embodiments, the cavity 110 may house a radiation generator 180 and a detector 170. The radiation generator 180 may emit radioactive rays. The radioactive rays may be transmitted to an object placed in the cavity 110 and received by the detector 170 after traversing the object. For example, the radiation generator 180 may include an X-ray tube. The X-ray tube may emit X-rays, which may traverse the object placed inside the cavity 110. The X-rays may be received by the detector 170 after traversing the object. In some embodiments, the detector 170 may include a circular detector, a square detector, an arc detector, etc. The arc detector may have a rotation angle ranging from 0 degree to 360 degree. In some embodiments, the rotation angle of the arc detector may be fixed. In some embodiments, the rotation angle of the arc detector may be adjusted based on demands. For example, the rotation angle of the arc detector may be adjusted according to an image resolution, an image size, a detector sensitivity, a detector stability as required, or the like, or a combination thereof. In some embodiments, the detector 170 may include a one-dimensional detector, a two-dimensional detector, a three-dimensional detector, etc.

The table 120 may support an object to be detected (e.g., a patient to be detected). In some embodiments, the table 120 may move inside the cavity 110 in a detection process. As shown in FIG. 1, the table 120 may move along the Z-axis direction in a detection process. According to detecting demands, the patient may be placed as supine, prone, or the head or the feet of the patient may be placed in the front. In some embodiments, the table 120 may move inside the cavity 110 at a constant speed. The moving speed of the table 120 may relate to a scan time, a scan region, etc. In some embodiments, the moving speed of the table 120 may be default settings of the system, or may be set by a user.

The high voltage generator 130 may generate a high voltage or a strong current. In some embodiments, the generated high voltage or strong current may be transmitted to the radiation generator 180. The generated high voltage may be from 80 kV to 140 kV, 75 kV to 150 kV, or 120 kV to 140 kV. The generated current may be form 20 mA to 500 mA.

The controller 120 may be connected to the cavity 110, the radiation generator 180, the detector 170, the high voltage generator 130, the table 120, the image generator 150, and/or the display device 160. The devices described above may be connected in a direct or indirect manner. In some embodiments, the controller 120 may control the cavity 110 to rotate to a certain position. The position may be default settings of the system, or may be set by a user (e.g., a doctor, a nurse, etc.). In some embodiments, the controller 120 may control the high voltage generator 130. For example, the controller 120 may control a voltage or a current intensity generated by the high voltage generator 130. In some embodiments, the controller 120 may control the display device 160. For example, the controller 120 may control a parameter relating to display. The parameter relating to display may include a display size, a display scale, a display order, a display quantity, etc. For example, the controller 120 may control a whole image or a part of the image to be displayed. As another example, the controller 120 may divide an image into several sub-images (e.g., a head sub-image, a neck sub-image and a lower limb sub-image) and display the several sub-images simultaneously or sequentially. As a further example, the controller 120 may magnify or diminish an image.

The image generator 150 may generate an image. In some embodiments, the image generator 150 may perform operations including an image preprocessing, an image reconstruction, and/or a blood vessel extraction, etc. The image generator 150 may be connected to the detector 170, the controller 120, the display device 160, and/or an external data source (not shown in FIG. 1). In some embodiments, the image generator 150 may receive data from the detector 170 or an external data source, and generate an image based on the received data. The external data source may include a hard disk, a floppy disk, a random access memory (RAM), a dynamic random access memory (DRAM), a static random access memory (SRAM), a bubble memory, a thin film memory, a magnetic plated wire memory, a phase change memory, a flash memory, a cloud disk, etc. In some embodiments, the image generator 150 may transmit the generated image to the display device 160 to be displayed.

The display device 160 may display received data or images. The display device 160 may be connected to the controller 120 and the image generator 150. In some embodiments, the display device 160 may display the image generated by the image generator 150. In some embodiments, the display device 160 may send instructions to the image generator 150 and/or the controller 120. For example, a user may set an imaging parameter via the display device 160. The imaging parameter may be transmitted to the controller 120. The imaging parameter may include a data collection parameter, an image reconstruction parameter, etc. The data collection parameter may include a scan time, location information of a scan target, a rotation speed of a gantry, a voltage/current intensity, or the like, or a combination thereof. The image reconstruction parameter may include a reconstruction field of view, a reconstruction matrix, a reconstruction algorithm, or the like, or a combination thereof.

It should be noted that this description of the imaging system 100 is intended to be illustrative, and is not intended to limit the scope of the present disclosure. For persons having ordinary skills in the art, after understanding the principle of the system, without departing the principle, may make any combination of the modules, or construct a sub-system connected with other modules, or may modify or change the forms and details of the application field in which the above method and system is applied.

Figure 2:
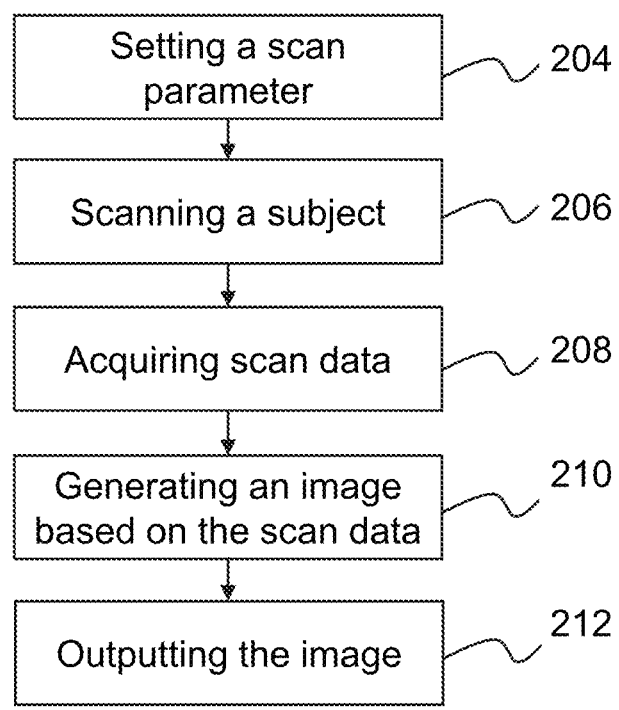
FIG. 2 is a flowchart illustrating an exemplary process for generating an image according to some embodiments of the present disclosure.

FIG. 2 is a flowchart illustrating an exemplary process for generating an image according to some embodiments of the present disclosure. In step 204, a scan parameter may be set. The process for setting the scan parameter may be performed by the controller 140. In some embodiments, the scan parameter may include a scan time, location information of a scan target, a position of a gantry, a rotation speed of the gantry, a voltage/current intensity, or the like, or a combination thereof. For example, the table 120 may be rotated to a specific position. As another example, the cavity 110 may be moved to a specific position. In some embodiments, the specific position may be default settings of the system, or may be set by a user (e.g., a doctor, a nurse, etc.). In some embodiments, the specific position may be set depending on different subjects. The subject may include a whole body of an object to be detected or a part of the object. The object to be detected may include a human body, an animal, a non-biological object, etc. For example, the subject may include an organ, a tissue, a lesion site, a tumor site, or the like, or a combination thereof. Specifically, for example, the subject may include a head, a chest, an abdomen, a heart, a liver, an upper limb, a lower limb, a spine, a bone, a blood vessel, or the like, or a combination thereof.

In step 206, a subject may be scanned. In step 208, scan data of the subject may be acquired. The scanning process and the process for obtaining scan data may be performed by the radiation generator 180 and the detector 170 jointly. In some embodiments, radioactive rays may traverse the subject and may be received by the detector 170 after being absorbed by the subject. In some embodiments, the radioactive rays may be reflected by the subject to the detector 170 and received by the detector. In some embodiments, at least one portion of the scan data may be acquired from an external data.

In step 210, an image may be generated based on the scan data. In some embodiments, the process for generating an image 210 may be performed by the image generator 150. The generated image may include an MRI image, a CT image, a PET image, or the like, or a combination thereof. For example, the CT image may be obtained by using a reconstruction algorithm. In some embodiments, the generated image may include a two-dimensional image or a three-dimensional image. In some embodiments, the generated image may be processed. The processing of the image may include a filtering for noise reduction, a gray normalization, a horizontal rotation, a size correction, etc.

In step 212, the image may be output. In some embodiments, the image may be displayed by the display device 160. In some embodiments, the image may be transmitted to an external device relating to the imaging system 100, such as a database, a terminal, etc.

It should be noted that the description of the process for generating the image is provided for the purposes of illustration, and is not intended to limit the scope of the present disclosure. For persons having ordinary skills in the art, after understanding the principle of the system, without departing the principle, may make any exchange or combination of the steps, or may modify or change the forms and details of the application field in which the above method and system is applied. For example, other selecting or processing conditions may be added between step 208 and step 210. For example, the acquired scan data may be stored for backups. Similarly, the operation of storing may be added between any two steps in the flowchart.

Figure 3:
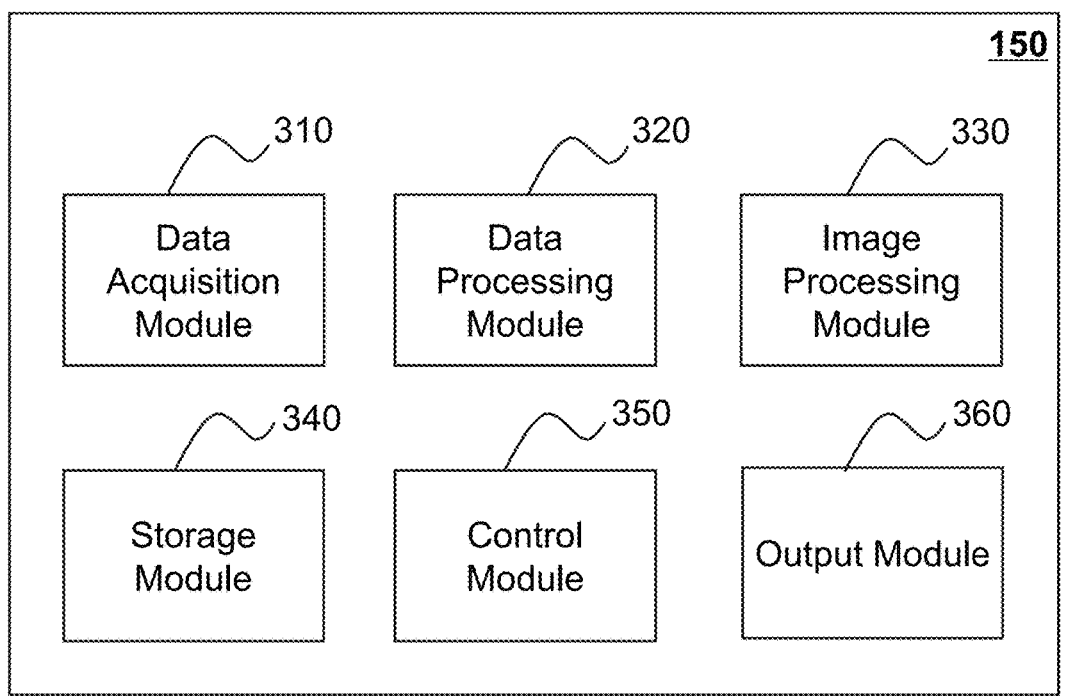
FIG. 3 is a block diagram illustrating an exemplary image generator according to some embodiments of the present disclosure.

FIG. 3 is a block diagram illustrating an exemplary image generator 150 according to some embodiments of the present disclosure. The image generator 150 may include a data acquisition module 310, a data processing module 320, an image processing module 330, a storage module 340, a control module 350, and an output module 360.

The data acquisition module 310 may receive data relating to a subject. The data relating to the subject may include scan data, basic information (e.g., name, age, gender, height, weight, medical history, etc.), a scan parameter, etc. In some embodiments, the scan data may be collected by the detector 170 and transmitted to the data acquisition module 310. In some embodiments, the scan data collected by the detector 170 may be transmitted to the storage module 340, and then transmitted to the data acquisition module 310 by the storage module 340. In some embodiments, the data acquisition module 310 may receive the scan parameter from the controller 120. In some embodiments, the data acquisition module 310 may receive the data (e.g., basic information of a patient) from an external data source (not shown in FIG. 3).

The data processing module 320 may analyze and process received data. The data processing module 320 may receive data from the data acquisition module 310, the storage module 340, and/or an external data source, and then analyze and process the data. In some embodiments, the data processing module 320 may preprocess the received data. For example, the data processing module 320 may process dark current and sweep data, remove defect dot(s), reduce noise(s), perform a geometric correction, etc. In some embodiments, the data processing module 320 may analyze and process the received scan data and generate an original image. As used herein, the original image may be an image generated based on scan data of a subject without preprocessing. In some embodiments, the data processing module 320 may perform a statistical analysis on the scan data and the basic information to generate a statistical result. For example, the data processing module 320 may count a probability of a specific group of people suffering from a specific disease. The statistical result may be transmitted to the storage module 340.

The image processing module 330 may generate an image and/or process the image. In some embodiments, the image processing module 330 may receive scan data processed by the data processing module 320 and generate an image based on the processed scan data. In some embodiments, the image processing module 330 may process an original image generated by the data processing module 320. The processing operation may include a filtering for noise reduction, a gray normalization, a horizontal rotation, a size correction, a removing of a part of shades (e.g., a removing of glasses), etc. In some embodiments, the image processing module 330 may reconstruct an image. For example, the image processing module 330 may perform an angiography. In some embodiments, the image processing module 330 may further analyze and process the generated image. For example, the image processing module 330 may extract a blood vessel in an image. For example, the image processing module 330 may control a parameter for extracting a blood vessel by the image processing module 330. The parameter may include a determination of a region of interest (ROI), a determination of a seed point, a determination of a centerline, etc. As used herein, the seed point may refer to an image voxel inside a blood vessel selected from an image. For example, the seed point may be an image voxel close to a center of a blood vessel. The centerline may refer to a line along the blood vessel and located inside the blood vessel. In some embodiments, a centerline of a blood vessel may refer to a collection of pixels located in or close to a central area of the blood vessel. In some embodiments, a centerline of a blood vessel may refer to a line connecting pixels with an equal distance or substantially equal distance to the boundary of the blood vessel.

The storage module 340 may store data, images, and/or correlation parameters, etc. The stored data may be data in various forms, for example, a numerical value, a signal, an image, information relating to a target, a command, an algorithm, a program, or the like, or a combination thereof. For example, scan data, an original image, a processed image, a processing parameter (e.g., a noise reduction parameter, a normalization parameter, etc.) may be stored in the storage module 340. In some embodiments, the storage module 340 may include a fixed storage system (e.g., a disk), a portable storage system (e.g., a USB interface, an interface for a FireWire port, etc., and/or a drive for a disk), etc. Specifically, in some embodiments, the storage module 340 may store an original image of a blood vessel, a processed image of the blood vessel, a setting parameter of an image of the blood vessel, etc. Further, the storage module 340 may store the data temporarily, that is, dump the data for next data processing. The storage module 340 may also store the data chronically, that is, store a final data processing result.

The control module 350 may control the data acquisition module 310, the data processing module 320, the image processing module 330, the storage module 340, and/or the output module 360. In some embodiments, the control module 350 may control a time point for receiving data and/or a path for transmitting data by the data acquisition module 310. In some embodiments, the control module 350 may control a speed of a data transmission, a mode of the data transmission (e.g., a real time transmission or a delay transmission), etc. In some embodiments, the control module 350 may control the image processing module 330 for reconstructing an image. For example, the control module 350 may select an algorithm for reconstructing an image. As another example, the control module 350 may control a parameter for extracting a blood vessel by the image processing module 330. The parameter may include a determination of a region of interest (ROI), a determination of a seed point, a determination of a centerline, etc. In some embodiments, the control module 350 may receive an instruction from a user (e.g., a doctor, an imaging engineer, etc.).

The output module 360 may output information. The information may include data, images, and/or correlation parameters, etc. The information may be from the data acquisition module 310, the data processing module 320, the image processing module 330, the storage module 340, and/or the control module 350. The information may be presented in various forms including an audio, a video, an image, a character, or the like, or a combination thereof. For example, the information may be broadcasted by a microphone, a loudspeaker, etc. As another example, the information may be displayed on a display screen. In some embodiments, the information may be data in various forms, including a numerical value, a signal, an image, correlation information of a target, a command, an algorithm, a program, or the like, or a combination thereof. For example, the information may include an original image of a blood vessel, a gray image of the blood vessel, a mask image of the blood vessel, a bulk processing image of the blood vessel, a precision processing image of the blood vessel, etc. As another example, the information may include a correlation parameter, such as, a histogram, a level set, a function set, etc. In some embodiments, the information may be output to any external device (e.g., a database, a terminal, etc.) relating to the imaging system 100. In some embodiments, the information may be displayed on any display device (e.g., the display device 160, a display screen of a computer, a display screen of a mobile phone, etc.).

In some embodiments, each module in the image generator 150 may include one or more general processors. The processor may include a programmable logic device (PLD), an application special integrated circuit (ASIC), a microprocessor, a system on chip (SoC), a digital signal processor (DSP), or the like, or a combination thereof. Two or more processors may be combined in one hardware device. The processor may implement data processing in various ways, such as, by a hardware, a software, or a combination thereof, etc.

It should be noted that the description of the image generator 150 is provided for the purposes of illustration, and is not intended to limit the scope of the present disclosure. For persons having ordinary skills in the art, after understanding the principle, without departing the principle, may modify or change the forms and details of the application field in which the above method and system is applied. For example, a storage unit may be added in each module of the image generator 150 for storing intermediate data or a processing result generated during an operation of each module. As another example, one or more modules may be integrated into one module which may implement functions of one or more modules. As still another example, the data acquisition module 310 and the image output module 360 may be integrated into one single module which may implement an input/output function simultaneously. As a further example, the control module 350 may be integrated into the image processing module 330 for controlling various parameters which may relate to an operation of the image processing module 330.

Figure 4:
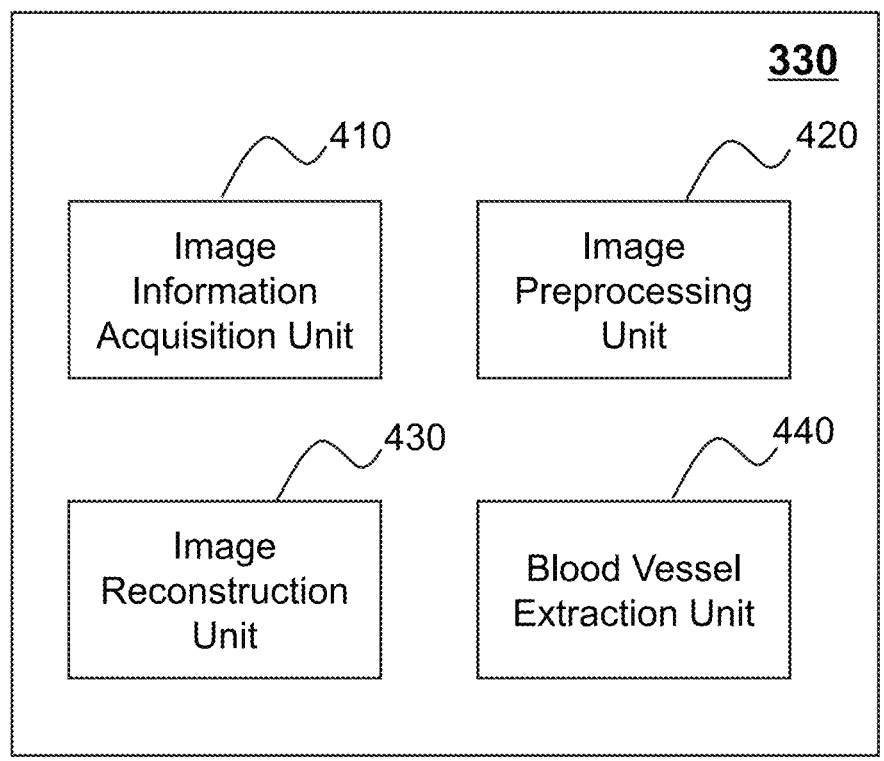
FIG. 4 is a block diagram illustrating an exemplary image processing module according to some embodiments of the present disclosure.

FIG. 4 is a block diagram illustrating an exemplary image processing module 330 according to some embodiments of the present disclosure. As shown in FIG. 4, the image processing module 330 may include an image information acquisition unit 410, an image preprocessing unit 420, an image reconstruction unit 430, and a blood vessel extraction unit 440.

The image information acquisition unit 410 may acquire original image information. The image information may be scan data which is used for generating an image or the image information may be a generated original image. In some embodiments, the image information acquisition unit 410 may acquire the scan data or the original image from the data processing module 320 or the storage module 340. In some embodiments, the image information acquisition unit 410 may transmit the received scan data or the original image to the image preprocessing unit 420 and/or the image reconstruction unit 430.

The image preprocessing unit 420 may perform a preprocessing operation on an image. The preprocessing operation may include a filtering for noise reduction, a gray normalization, a horizontal rotation, a size correction, a removing of a part of shades (e.g., a removing of glasses), etc. For example, the image preprocessing unit 420 may perform a filtering smoothing operation on an original image to reduce noise(s) in the image.

The image reconstruction unit 430 may reconstruct an image. In some embodiments, the image reconstruction unit 430 may reconstruct an image based on scan data. In some embodiments, the image reconstruction unit 430 may perform a two-dimensional reconstruction or a three-dimensional reconstruction. In some embodiments, an algorithm for reconstructing an image may include a filtered back projection (FBP), an ordered subsets expectation maximization (OSEM), an FDK algorithm, or the like, or a combination thereof. In some embodiments, the image reconstruction unit 430 may transmit the image to the image preprocessing unit 420 and/or the blood vessel extraction unit 440 for further processing.

The blood vessel extraction unit 440 may extract a blood vessel from an image. In some embodiments, a blood vessel may be extracted from a head, a cervix, an abdomen, a lower limb, etc. An algorithm for blood vessel extraction may include a pattern recognition algorithm, a model algorithm, a tracking algorithm, an artificial intelligence algorithm, a neural network algorithm, a tubular detection algorithm, etc. In some embodiments, the blood vessel extraction unit 440 may determine a region of interest (ROI) for extracting a blood vessel, a seed point of a target blood vessel, a centerline, a specific portion of a blood vessel (e.g., a venous sinus), etc. In some embodiments, the blood vessel extraction unit 440 may extract a blood vessel based on a level set, a region growing, an MS model, a CV model, etc. In some embodiments, the blood vessel extraction unit 440 may separate a boundary of a blood vessel. For example, the boundary of the blood vessel may be determined based on a data expansion operation and/or a data erosion operation. As another example, the boundary of the blood vessel may be separated by using multi-level model boundary parameters.

It should be noted that the description of the image processing module 330 is provided for the purposes of illustration, and is not intended to limit the scope of the present disclosure. For persons having ordinary skills in the art, after understanding the principle, without departing the principle, may modify or change the forms and details of the application field in which the above method and system is applied. However, those variations and modifications may not depart from the protecting of the present disclosure. For example, the image preprocessing unit 420 may be integrated into the image reconstruction unit 430 for implementing functions of image reconstruction and image preprocessing. As another example, the blood vessel extraction unit 440 may be integrated into the image reconstruction unit 430 for extracting a blood vessel directly from a reconstructed image.

FIG. 5-A is a block diagram illustrating an exemplary blood vessel extraction unit 440 according to some embodiments of the present disclosure. As shown in FIG. 5, the blood vessel extraction unit 440 may include a separation sub-unit 510, an extraction sub-unit 520, and a feature extraction sub-unit 530.

The separation sub-unit 510 may determine a region of interest (ROI). The ROI may be a region including a blood vessel. The shape of the ROI may include a tube, a ring, a circle, an oval, a triangle, a rectangle, an irregular shape, etc. In some embodiments, the shape of ROI may relate to a physiology-anatomy structure of a target blood vessel or the region where the target blood vessel is located. For example, an ROI of a cerebral artery may be tubular. In some embodiments, the separation sub-unit 510 may determine an ROI by a template registration. For example, an image to be processed may be registered with a corresponding template to determine an ROI. In some embodiments, the ROI may be determined by a multi-template registration. For example, according to physiological structure, an image may be divided into different regions, such as, a head, a cervix, an abdomen, a lower limb, etc., and then images to be processed of different regions may be registered with templates corresponding to the regions to determine ROIs in each of the regions. In some embodiments, the separation sub-unit 510 may determine an ROI by using a classifier. For example, image features (e.g., a gray value of an image, a gradient value of the image, an enhanced value of the image, a shape, etc.) may be extracted, and the image features may be analyzed by using a classifier to determine the ROI.

The extraction sub-unit 520 may extract a target blood vessel. The target blood vessel may include a blood vessel in head-neck area, an abdominal blood vessel, a lower limb blood vessel, etc. The blood vessel in head-neck area may include a vertebral artery, a basilar artery, an internal carotid, etc. The abdominal blood vessel may include an abdominal aorta, a renal artery, a hepatic vein, etc. In some embodiments, the extraction sub-unit 520 may further determine a seed point of a blood vessel and/or a centerline of the blood vessel, etc. For example, the extraction sub-unit 520 may determine a seed point of a blood vessel according to a physiological structural property (such as, symmetry) of the blood vessel. As another example, the extraction sub-unit 520 may determine a centerline of the blood vessel based on the seed point of the blood vessel. As a further example, the extraction sub-unit 520 may determine a starting point, a path point, and an end point of the blood vessel, and connect these points to determine the centerline of the blood vessel. As a still further example, the extraction sub-unit 520 may further select a line in the extracted blood vessel as the centerline of the blood vessel. In some embodiments, the extraction sub-unit 520 may perform a blood vessel enhancement operation on the blood vessel image to obtain an enhanced blood vessel image. In some embodiments, the extraction sub-unit 520 may extract the blood vessel in the enhanced blood vessel image. In some embodiments, the extraction sub-unit 520 may segment (also referred to as "extract") a blood vessel based on an iterative technique. For example, the extraction sub-unit 520 may divide blood vessels into different regions to guarantee that there is only one complete main blood vessel in one region; the extraction sub-unit 520 may segment main blood vessels in each of the regions; the extraction sub-unit 520 may further detect whether the blood vessel segmentation is segmented; if the extraction sub-unit 520 determines that the blood vessel is not segmented, the extraction sub-unit 520 may select other alternative segmentation techniques in an iterative mode until the blood vessel is segmented.

The feature extraction sub-unit 530 may extract a specific portion from an extracted blood vessel. The specific portion may include a blood vessel with a specific type or a part of a blood vessel. For example, a specific portion of a blood vessel may include a venous sinus in the blood vessel. The feature extraction sub-unit 530 may extract the venous sinus from an extracted blood vessel tree. Specifically, in some embodiments, the feature extraction sub-unit 530 may divide the extracted blood vessel into multiple regions, determine a specific region, determine a connected component where the venous sinus is located in the specific region, perform a dilation and a region growth in the connected domain, and extract the venous sinus.

FIG. 5-B is a flowchart illustrating an exemplary process for extracting a blood vessel according to some embodiments of the present disclosure. In some embodiments, the extraction of a blood vessel may be performed by the blood vessel extraction unit 440. In step 502, an image may be acquired. The image may include a two-dimensional image or a three-dimensional image. In some embodiments, the image may include an image output by the image preprocessing unit 420 and/or the image reconstruction unit 430.

In step 504, a region of interest (ROI) for extracting a blood vessel may be determined. The ROI may include a region where the blood vessel is located. The shape of the ROI may include a tubule, a ring, a circle, an oval, a triangle, a rectangle, an irregular shape, etc. For example, an ROI of a cerebral artery may be tubular. In some embodiments, the ROI may be determined by a template registration. For example, an image to be processed may be registered with a corresponding template to determine the ROI. In some embodiments, the ROI may be determined by a multi-template registration. For example, according to physiological structure, an image may be divided into different regions, such as, a head, a cervix, an abdomen, a lower limb, etc., and then the images to be processed of different regions may be registered with templates corresponding to the regions to determine the ROIs in each of the regions. In some embodiments, the ROI may be determined by using a classifier. For example, image features (e.g., a gray value of an image, a gradient value of an image, an enhanced value of an image, a shape, etc.) may be extracted, and the image features may be analyzed by using a classifier to determine the ROI. In some embodiments, the ROI may be determined by a machine learning technique (e.g., a machine learning model). For example, the machine learning model may include one or more parameters relating to the determination of the ROI. The machine learning model may be trained by historical data to determine the parameters. The ROI may be further determined based on the parameters.

In step 506, a blood vessel may be extracted. In some embodiments, a centerline of a blood vessel may be determined in advance, and the blood vessel may be grown based on the centerline of the blood vessel. In some embodiments, the blood vessel may be extracted by constructing a blood vessel model. In some embodiments, the blood vessel may grow in the ROI based on a feature (e.g., gray values) of the blood vessel. In some embodiments, the blood vessel may be extracted based on a machine learning technique. In some embodiments, a blood vessel tree may also be determined according to the extracted blood vessel.

In some embodiments, whether the blood vessel has been successfully segmented may be further detected. If not, the blood vessel may be re-segmented by using an alternative segmentation technique until the segmentation is successfully performed. The alternative segmentation technique may include a segmentation technique relating to an aneurysmal blood vessel, a segmentation technique relating to a blood vessel with a low dose contrast agent, or a segmentation technique relating to a calcific malformation blood vessel. According to the segmentation technique relating to the aneurysmal blood vessel, the blood vessel may be extracted based on a gray and a gradient threshold by using a level set algorithm with no shape constraint. According to the segmentation technique relating to the blood vessel with the low dose contrast agent, a method based on a blood vessel model may be used. In the method, a shape constraint may be added on the basis of image features, such as, gray, gradient, etc. According to the segmentation technique relating to the calcific malformation blood vessel, the blood vessel may be extracted synthetically based on image features, such as, gray, gradient, shape constraint, etc.

In step 508, a specific portion of the blood vessel may be extracted. The specific portion of the blood vessel may include a blood vessel with a specific type or a part of the blood vessel. For example, a venous sinus may be extracted from the determined blood vessel tree based on physiology-anatomy properties of the venous sinus (e.g., a size, a shape, a position, etc.).

It should be noted that the description of extracting a blood vessel is provided for the purposes of illustration, and not intended to limit the scope of the present disclosure. For persons having ordinary skills in the art, after understanding the principle, without departing the principle, may modify or change the forms and details of the application field in which the above method and system is applied. However, those variations and modifications may not depart from the protecting of the present disclosure. For example, one or more optional operations may be added between step 504 and step 506, for example, a step of determining a centerline of the blood vessel, a step of determining a seed point of the blood vessel. As another example, step 508 may be not necessary. The specific portion of the blood vessel may be extracted or not extracted according to actual demands.

Figure 6:
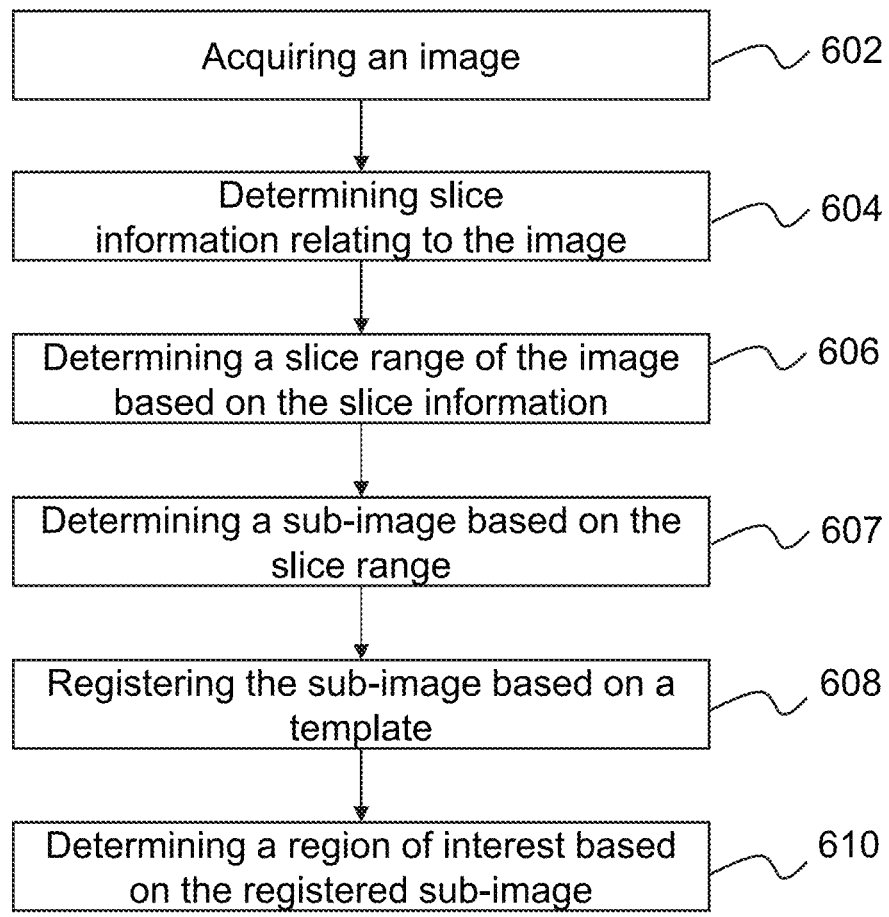
FIG. 6 is a flowchart illustrating an exemplary process for determining a region of interest (ROI) according to some embodiments of the present disclosure.

FIG. 6 is a flowchart illustrating an exemplary process for determining a region of interest (ROI) according to some embodiments of the present disclosure. In some embodiments, the determination of an ROI may be performed by the separation sub-unit 510. In step 602, an image may be acquired. The image may include different physiological regions, such as, a head, a cervix, an abdomen, a lower limb, etc. The image may include a two-dimensional or a three-dimensional image. In some embodiments, the image may be a computed tomography angiography (CTA) image. In some embodiments, the image may be an image output by the image preprocessing unit 420 and/or the image reconstruction unit 430.

In step 604, slice information may be identified. As used herein, the slices may refer to N slices of an image arranged in a certain sequence (e.g., from head to feet), wherein N is any positive integer. The value of N may be default settings of the system, or may be set by a user (e.g., a doctor, a nurse, etc.). In some embodiments, different subjects (e.g., different patients) may correspond to different values of N. For example, the system may determine a required scan range to determine the value of N according to physiological information of the subject (e.g., height, weight, etc.). In some embodiments, one of the N slices may be selected and the slice information may be identified. The slice information may include a size of a slice, a shape of the slice, a position of the slice, etc. In some embodiments, a region to which the slice belongs may be determined according to the slice information. For example, whether the slice belongs to a vertex, a half head, a skull base, etc., may be determined according to the size and/or the shape of the slice.

In step 606, a slice range of a sub-image may be determined based on the slice information. As used herein, the sub-image may correspond to a part of the image, such as, a head sub-image, a neck sub-image, an abdomen sub-image, etc. For example, the slice range of the sub-image may be determined according to the identified slice position information (such as, a vertex, a half head, a skull base, etc.). For example, if the selected slice in step 604 is the second slice and the identified slice information is the head, the slice range of the head sub-image may be determined as from the third slice to the ninth slice. In 607, the sub-image may be determined based on the determined slice range. For example, the head sub-image may be determined based on the slice range.

In step 608, the sub-image may be registered based on a template. In some embodiments, the template may be a standard image template. In some embodiments, N cases may be acquired from any storage device (e.g., a database) described in the disclosure, and a composite statistics may be performed on data of the N cases. Further, the standard image template may be generated by registering, fusing, and/or labeling manually by a doctor, etc. For example, head images and neck images of a plurality of patients may be determined respectively with the position of a foramen magnum and the position of an atlas as a boundary. A head image template and a neck image template may be generated by registering, filtering, averaging, etc. In some embodiments, the templates may be generated based on an average population. For example, if an image to be processed is from a certain patient, images (also referred to as "reference images") of multiple reference cases similar to or relating to the patient in age, gender, body size, anatomical location of an ROI, disease prediction, etc., may be searched in a database. The image templates may be generated based on the reference images and the related information. For example, an ROI of a reference case may be determined, and the ROI may be marked as an ROI mask (also referred to as "membrane" or "mask"). Images of multiple reference cases may correspond to multiple different masks. The ROI may be marked automatically, manually, etc. The marking process may refer to that a specific part of an image may be blocked or covered and then the specific part of the image may be extracted. Then, according to a mapping relationship (e.g., a deformation field based on an affine registering relation matrix and a non-rigid body registration), the mask of the ROI in each of the reference cases may be mapped to a coordinate space, for example, a coordinate space of an reference image, and a probability distribution of the ROIs may be determined. Further, information corresponding to the ROIs in the multiple reference cases may be combined to obtain a probability graph (or an information profile). In some embodiments, a probability value of a pixel in the probability graph may represent a position probability (i.e. a probability that the position is the target region) of a target region (i.e. an ROI where a blood vessel is located in). In some embodiments, a probability value of a pixel in the probability graph may be in a range from 0 to 1. In some embodiments, the greater a probability value of a pixel is, the greater a gray value of the pixel is, and the greater a position probability of a target region is. In some embodiments, a probability range of the probability graph may be adjusted. For example, a probability range of the information profile of a target region may be adjusted from more than 0 to more than 0.25 to reduce a searching region.

In some embodiments, multi-templates may be used to register. For example, an image may be divided to a head sub-image and a neck sub-image dynamically. The head sub-image and the neck sub-image may be registered with corresponding regional image templates. The region may refer to a sub-region of a patient, such as, a head, a cervix, an abdomen, a lower limb, etc. In some embodiments, the registering process may be combined with anatomical features of the region, information for clinical diagnosis of the region, etc. For example, a region where an internal carotid is located may be determined preliminarily according to anatomical features of a neck. In some embodiments, a suitable registering technique or a spatial transformation model may be selected dynamically.

In step 610, an ROI may be determined based on the registered sub-image. In some embodiments, a combined ROI may be determined based on the determined ROIs of the sub-images. For example, a head ROI and a neck ROI may be combined to obtain an ROI of a head-neck area.

Figure 7:
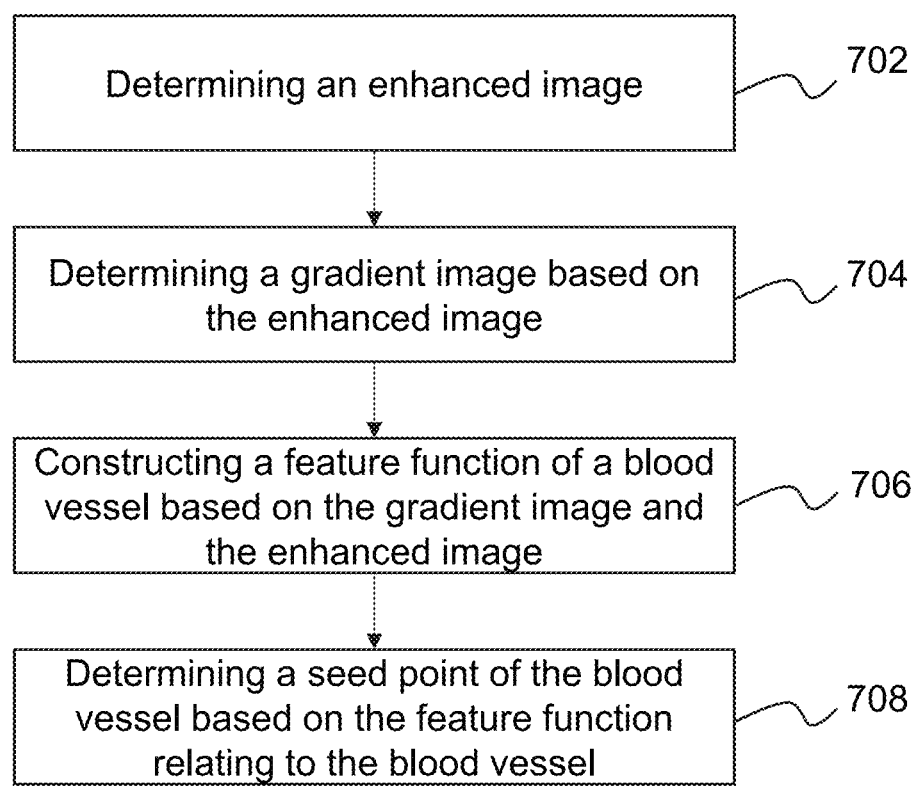
FIG. 7 is a flowchart illustrating an exemplary process for determining a seed point of a blood vessel according to some embodiments of the present disclosure.

FIG. 7 is a flowchart illustrating an exemplary process for determining a seed point of a blood vessel according to some embodiments of the present disclosure. In some embodiments, the seed point of the blood vessel may be determined by the extraction sub-unit 520. In some embodiments, the seed point of the blood vessel may be determined before extracting the blood vessel. In some embodiments, the seed point of the blood vessel may be determined after determining an ROI.

In step 702, an enhanced image may be determined. As used herein, the enhanced image may refer to an image obtained after enhancing the image where a target blood vessel is located. In some embodiments, the image may be enhanced based on a Hessian matrix to obtain the enhanced image. In some embodiments, a preprocessing operation may be performed on the image before determining the enhanced image. For example, gray values of connected components in an image where a middle cerebral artery is located may be determined, and connected component(s) with gray value(s) larger than a gray threshold may be removed. In some embodiments, the gray threshold may be default settings of the system, or may be set by a user.

In step 704, a gradient image may be determined based on the enhanced image. The gradient image may include gradient information of the image, such as, gradient values. The gradient values may reflect a change degree of gray values of the pixels in the image. For example, the greater a gradient value is, the more significant the gray value change of pixels in the image is.

In step 706, a feature function of a blood vessel may be constructed based on the enhanced image and the gradient image. The feature function of the blood vessel is constructed based on image features. The image features may include a gray value, a gradient value, an enhanced value, a shape, or the like, or a combination thereof. In some embodiments, an ROI may be divided into two symmetric regions based on symmetry of the blood vessel. In some embodiments, the feature function of the blood vessel may include one or more variables relating to the symmetry of the blood vessel. For example, the variables may include image features of the two symmetric regions. In some embodiments, the feature functions of the blood vessel may be constructed respectively for the two symmetric regions. For example, a feature function of a left blood vessel and a feature function of a right blood vessel may be constructed respectively. In some embodiments, the feature function of the blood vessel may be represented by Equation (1) as illustrated below:

$$F_i = f(G_i, T_i, H_i, S_i), \quad (1)$$

where i refers to l or r, wherein l denotes a left side, r denotes a right side; G denotes a gray value, T denotes a gradient value, H denotes an enhanced value, and S denotes a shape index.

In some embodiments, the feature function of the left blood vessel and the feature function of the right blood vessel may be further determined based on symmetry to obtain a total feature function of the blood vessel, as illustrated by Equation (2):

$$F = (F_l * F_r)/d_z, \quad (2)$$

where $F_l$ denotes a feature function of the left blood vessel, $F_r$ denotes a feature function of the right blood vessel, and $d_z$ denotes a distance between left-right symmetrical blood vessel points in the Z direction.

In step 708, a seed point of the blood vessel may be determined based on the feature function of the blood vessel. In some embodiments, the seed point of the blood vessel may be determined based on a function value of the feature function of the blood vessel determined in 706. For example, a pair of left-right symmetrical points with maximum values of the feature function may be determined as a seed point of a target blood vessel.

It should be noted that the description of extracting a seed point is provided for the purposes of illustration, and not intended to limit the scope of the present disclosure. For persons having ordinary skills in the art, after understanding the principle, without departing the principle, may modify or change the forms and details of the application field in which the above method and system is applied. However, those variations and modifications may not depart from the protecting of the present disclosure. For example, in some embodiments, the determination of a seed point of the blood vessel may be not necessary. For another example, after determining a seed point of the blood vessel, a corresponding blood vessel may be extracted further based on the seed point of the blood vessel. Further, a centerline of the blood vessel centerline may be determined after determining the seed point of the blood vessel.

FIG. 8-A is a flowchart illustrating an exemplary process for training a strong classifier according to some embodiments of the present disclosure. In some embodiments, the process for training a strong classifier may be performed by the extraction sub-unit 520. In some embodiments, the strong classifier may be trained based on Adaboost. In 802, training samples may be collected. The training samples may include positive training samples (also referred to as "positive sample points") and negative training samples (also referred to as "negative sample points"). In some embodiments, points inside the blood vessel in an image template (as described in connection with FIG. 6) may be selected as positive sample points, and several points in a region around the blood vessel may be randomly selected as negative sample points. For example, a mask operation may be performed on the blood vessel to obtain a blood vessel mask Mask0. Then, a dilation operation may be performed on the blood vessel mask Mask0 to expand the edge of the blood vessel mask Mask0 to obtain a blood vessel mask Mask1. The dilation operation may be a process in which all background points contacting an object (e.g., a blood vessel) may be incorporated into the object and the boundary of the object may be expanded outward. An "OR" operation may be further performed on the blood vessel mask Mask1 and Mask0 to exclude the same points in the Mask1 and Mask0 to extract and obtain different points. The regions where the different points are located may be the regions around the blood vessel. In some embodiments, the positive sample points and the negative sample points may be collected inside and around the blood vessel respectively. The amounts of the positive sample points and the negative sample points may be random. The amounts of the positive sample points and the negative sample points may be inconsistent. For example, the amount of the positive sample points may be more than that of the positive sample points.

In step 804, weak classifiers may be determined by training the training samples. Firstly, the positive sample points and the negative sample points may be acquired to initialize a weight distribution of the training samples. In some embodiments, each sample point may be assigned with a same weight value. A first weak classifier may be obtained by training the training samples according to the initialization of the weight distribution. Then, whether the positive and negative sample points are accurately classified may be determined. If a sample point is classified accurately, the weight value of the sample point may be decreased in a next training; in contrast, if a sample point is not classified accurately, the weight value of the sample point may be increased in the next training. The m is-classified sample points in the first training may be highlighted to obtain a new sample distribution through the above operations. In some embodiments, the weak classifier may be assigned to a weight which may represent the importance of the weak classifier according to the classification error. The fewer the classification error is, the greater the weight may be.

The samples may be trained again based on the new sample distribution to obtain a next weak classifier and a weight thereof. The sample distribution may be further changed for training the samples to obtain a series of weak classifiers until a predetermined classification error or a preset maximum iterative threshold may satisfy. For example, if the preset iterative threshold is T, T weak classifiers and weights corresponding to the T weak classifiers may be obtained after T times of iterations.

In step 806, a strong classifier may be determined by combining the weak classifiers. The strong classifier may be determined by superimposing the series of weak classifiers determined in 804 according to the weights. The strong classifier may be represented by Equation (3):

$$h(x) = \begin{cases} 1 & \sum_{t=1}^{T} \alpha_t h_t(x) \geq \frac{1}{2}\sum_{t}^{T} \alpha_t, \\ 0 & \text{otherwise} \end{cases} \quad (3)$$

where $h_t(x)$ denotes a weak classifier, $\alpha_t$ denotes a weight corresponding to each weak classifier indicating a performance of the weak classifier. The smaller weight may represent that the weak classifier may play a relatively small role in the final strong classifier, and the larger weight may represent that the weak classifier may play a relatively large role in the final strong classifier. Although the classification accuracy of a single weak classifier is not high, the classification accuracy may be effectively improved by assigning the weak classifiers with different weights. The strong classifier finally obtained may be stored in any storage device described in the disclosure to be further used in the extraction of a centerline of a blood vessel.

FIG. 8-B is a flowchart illustrating an exemplary process for determining a centerline of a blood vessel according to some embodiments of the present disclosure. In some embodiments, the process for determining a centerline of a blood vessel may be performed by the extraction sub-unit 520. In step 808, an image may be registered as described in connection with FIG. 6 to determine an ROI. In step 810, an enhanced image relating to the blood vessel may be determined based on a strong classifier. The strong classifier may be acquired from any storage device describe in the disclosure. In some embodiments, the strong classifier may be obtained by combining a plurality of weak classifiers (as illustrated in FIG. 8-A). The enhanced image herein may refer to an image obtained by enhancing the region where a target blood vessel is located. The enhanced image of the blood vessel may be determined according to Equation (4):

$$\text{Vesselness}(x) = \sum_{t=1}^{T}\alpha_t h_t(x), \quad (4)$$

where $h_t(x)$ denotes a weak classifier, $\alpha_t$ denotes a weight corresponding to each weak classifier, and Vesselness (x) denotes an enhanced value of the blood vessel.

As illustrated in Equation (4), when the blood vessel enhanced value of a certain point is greater than a preset threshold $\frac{1}{2}\sum_{t}^{T}\alpha_t$, the point may be determined as a point in the blood vessel; when the blood vessel enhanced value of a certain point is lower than the threshold, the point may be determined as a point not in the blood vessel. The enhanced image of the blood vessel may be obtained according to the determination result.

In step 812, a centerline of a blood vessel may be determined based on the enhanced image of the blood vessel. The centerline of the blood vessel may refer to a line located in and along the blood vessel. In some embodiments, the centerline of the blood vessel may refer to a collection of pixels located in or close to a central area of the blood vessel. In some embodiments, the centerline of the blood vessel may refer to a line connecting pixels with an equal distance or substantially equal distance to the boundary of the blood vessel. In some embodiments, the centerline of the blood vessel may be determined based on a fast marching algorithm.

In some embodiments, a transformation image may be determined based on the enhanced image of the blood vessel obtained in step 810. The transformation image may be determined according to Equation (5) as illustrated below:

$$P_{i,j,k} = (\text{Grad}(x) + \text{fabs}(\text{Std}(x) - \text{Std}(x_0)))/\text{Vesselness}(x), \quad (5)$$

where i, j, k denote a pixel, Grad(x) denotes a gradient value of a current point, Std(x) denotes a variance among the current point and neighborhood points, $\text{Std}(x_0)$ denotes a variance corresponding to a seed point, and Vesselness(x) denotes the blood vessel enhanced value of the current point.

Further, a level set function field may be established according to the transformation image. In some embodiments, an evolution function may be obtained by inserting a moving curve as a zero level set into a higher dimension function based on a level set method. For example, an evolution of a two-dimensional curve may be converted into an evolution of a three-dimensional surface, and an evolution equation of the three-dimensional surface evolution may be obtained by an evolution equation of the two-dimensional curve evolution. Further, a position of a point set of the evolution function on the zero level interface may be acquired and the evolution result of a moving curve may be determined. Specifically, a function field of a level set may be firstly initialized to establish an initialized curve based on the above transformation image. In some embodiments, the seed point of the blood vessel may be determined as an original curve, the level set function and the zero level set may be updated continuously in an evolution process, and an evolution curve corresponding to the zero level set of the level set function may be finally obtained. The level set technique may be described in, for example, "Level set methods and fast marching methods: evolving interfaces in computational geometry, fluid mechanics, computer vision, and materials science" by J. A. Sethian, published by Cambridge University Press, 1999, the contents of which are hereby incorporated by reference.

For example, original curves of level set function fields corresponding to a starting seed point and an ending seed point may be set based on the determined seed points of the blood vessel (e.g., the seed points of the blood vessel determined as illustrated in FIG. 7). The two level set function fields may continuously evolve with time. The smaller the P value of the pixel in Equation (5) is, the shorter the time from the initial curve to the pixel may be, that is, the level set function field may change faster along the pixel with a smaller P value (i.e., a pixel more similar to the blood vessel). In some embodiments, the evolution equation of a level set function field may be represented by Equation (6):

$$P_{i,j,k}^2 = (\max\{u - U_{i-1,j,k}, u - U_{i+1,j,k}, 0\})^2 + (\max\{u - U_{i,j-1,k}, u - U_{i,j+1,k}, 0\})^2 + (\max\{u - U_{i,j,k-1}, u - U_{i,j,k+1}, 0\})^2, \quad (6)$$

where $U_{i,j,k}$,u denotes a level set function field corresponding to a point and $U_{i,j,k}$,0 denotes a zero level set function field. With the two level set function fields continuously evolving, an intersection point of the two level set function fields may occur in a faster path. The intersection point may be a point on the blood vessel. Further the centerline of the blood vessel between the starting seed point and the ending seed point may be determined by tracing back the two seed points from the intersection point based on a steepest descent method.

A similarity degree value of each pixel or voxel in the enhanced image of the blood vessel may be determined based on the blood vessel features. In the enhanced image of the blood vessel acquired in the above operations, for example, image features (e.g., a gray value, a gradient value, an enhanced value, a shape, etc.) may be extracted. Taking the seed point as a starting point, the similarity P values among neighbor points may be analyzed according to the blood vessel features. The similarity P value may be determined according to Equation (7):

$$P_{i,j,k} = \frac{(Grad(x) + |Std(x) - Std(x_0)|)}{Vessel(x)}, \quad (7)$$

where Grad(x) denotes a gradient value of a current point, Std(x) denotes a variance among the current point and the neighbor points, $Std(x_0)$ denotes a variance corresponding to the seed point of the blood vessel, and Vessel(x) denotes the blood vessel enhanced value corresponding to the point in the enhanced image of the blood vessel acquired according to Equation (4). Because the structure inside the blood vessel may be uniform, gradient values of pixels inside the blood vessel may be relatively small and variances of the pixels may be relatively small, and absolute values of the difference values between the variances and the variances corresponding to the seed point $|Std(x)-Std(x_0)|$ also may be relatively small. Therefore, the smaller the P value of a pixel in Equation (7) is, the more the pixel may be similar to the blood vessel, that is, the shorter the time from the seed point as a starting point to the pixel (or the shorter the energy) is, the shorter the distance from the seed point to the pixel represented in the image may be. It should be noted that Equation (7) is an exemplary embodiment of the present disclosure, the gradient value Grad(x) and the variance Std(x) may be replaced according to the blood vessel features and an equivalent effect may be obtained.

Figure 17:
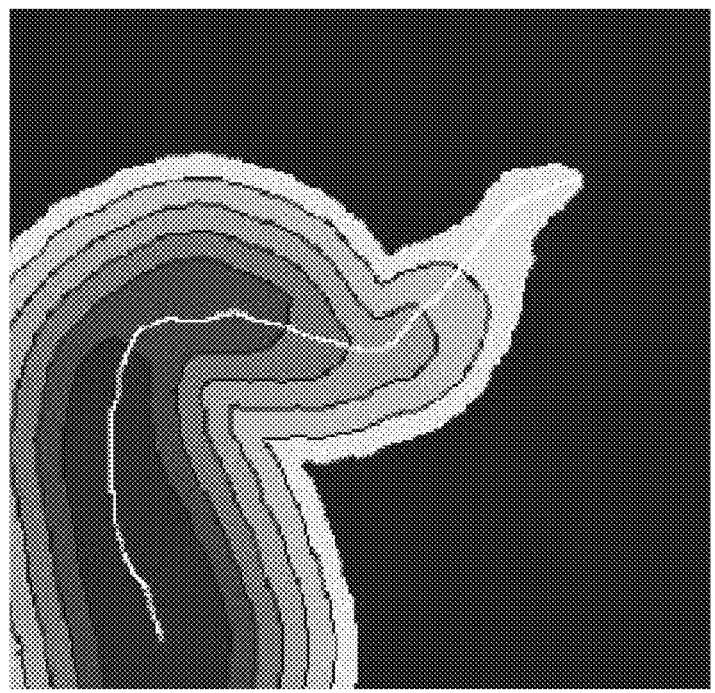
FIG. 17 is an exemplary image illustrating a U field according to some embodiments of the present disclosure.

A U field may be obtained according to the similarity P value. The U value in the U field may be determined according to Equation (8):

$$(\max\{u-U_{i-1,j,k}, u-U_{i+1,j,k}, 0\})^2 + (\max\{u-U_{i,j-1,k}, u-U_{i,j+1,k}, 0\})^2 + (\max\{u-U_{i,j,k-1}, u-U_{i,j,k+1}, 0\})^2 = P_{i,j,k}^2 \quad (8)$$

where u denotes a viscosity solution constant, and the U value denotes a minimum energy value required by two seed points to pass through a point (i, j, k). The P value of the point (i, j, k) determined according to Equation (7) may be substituted into Equation (8) to obtain the U value of the point. The U value of each point in a region of the blood vessel may be obtained and the U field may be determined as illustrated in FIG. 17.

FIG. 8-C is a flowchart illustrating an exemplary process for determining a centerline of a blood vessel according to some embodiments of the present disclosure. In some embodiments, the process for extracting a centerline of a blood vessel may be performed by the extraction sub-unit 520. In step 820, multiple sample images may be registered. For example, blood vessels in the sample images may be extracted. Then one of the sample images may be taken as a template image. The residual other images may be registered based on the template image. For example, a binary image registration may be performed on the blood vessel. In some embodiments, the sample images may be default settings of the system, or may be determined by a user. For example, the type of the sample image may be the same with an image to be processed. For example, if the image to be processed is a head image, the sample image may also be a head image.

In step 822, centerlines of blood vessels may be extracted from the sample images (also referred to as "reference centerlines of blood vessels"). Pixels on centerlines of the blood vessels may be sampled to obtain a plurality of centerline sample points. In some embodiments, assuming that there are M sample images, M centerlines of blood vessels in the M sample images may correspond to M training samples. Each of the training samples may include a plurality of centerline sample points.

In step 824, an average model of the centerline of the blood vessel may be generated. In some embodiments, the average model of the centerline of the blood vessel may be extracted from the centerline sample points by using an active shape model (ASM) algorithm. The ASM algorithm herein may be used to acquire statistical information of a distribution of the sample points in the sample images by training the sample images based on a point distribution model. Further, possible change directions of the sample points may also be acquired and feature points corresponding to the sample points may be determined in the image to be processed.

In some embodiments, the centerline of the blood vessel in each sample image may correspond to a centerline shape vector. Multiple centerline shape vectors corresponding to the multiple centerlines of blood vessels in the multiple sample images may constitute a training set. In some embodiments, an alignment operation may be performed on the centerline shape vectors corresponding to the centerlines of blood vessels extracted from the sample images. The alignment operation herein may reduce the non-shape interfere caused by external factors such as different sizes of images, distances, etc., such that the corresponding points in different samples may have a comparability.

For example, the alignment operation may include: 1. selecting a sample from M training samples as a reference sample, determining the centerline shape vector of the reference sample as a reference shape vector, and aligning all the centerline shape vectors in the training set to the reference sample shape vector; 2. determining an average centerline shape vector; 3. aligning all the centerline shape vectors to the average centerline shape vector to further determine a new average centerline shape vector; 4. aligning all the centerline shape vectors to the new average centerline shape vector. An average model of the centerline may be obtained by repeating the above operations until the convergence is reached.

Further, in some embodiments, a principal direction and rule of shape changes may be obtained by using a principal component analysis (PCA) method after the alignment operation is performed on the centerline shape vector. A covariance matrix of data may be determined based on the average shape vector. The eigenvalues and eigenvectors of the covariance matrix may be further determined. And the eigenvalues may be sorted in the descending order. The first k eigenvalues and the corresponding eigenvectors of the covariance matrix may be extracted by using the PCA method. Further, a statistical shape model of the training samples may be constructed according to the eigenvalues and the eigenvectors and a shape parameter may be obtained which may be used for controlling the shape changes of the sample points.

In step 826, the centerline average model may be mapped to an image to be processed to obtain a centerline of a blood vessel in the image to be processed. In some embodiments, a preliminary blood vessel segmentation based on a threshold may be performed on the image to be processed to segment a rough outline and edges of the blood vessel to obtain a preliminary segmentation result of the blood vessel. A preliminary threshold segmentation may also be performed on the template image. A binary image of the template image may be registered with a binary image of the image to be processed, and the centerline average model of may be mapped to the image to be processed.

In step 828, a boundary distance field may be set. The distance field may refer to that a distance value may be defined for one or more pixels in an image to form a distance field. In some embodiments, a distance value may be determined for each feature point on the centerline of the blood vessel of the image to be processed obtained by mapping based on the edges of the blood vessel obtained through the preliminary segmentation. Specifically, a blood vessel may include a left edge and a right edge, for a specific feature point, there may be two distance values including a distance value from the left edge and a distance value from the right edge respectively, and the smaller one may be selected as the distance value of the specific feature point. The distance value in the distance field may reflect the distance from the point to the center of the blood vessel. In a preset distance field, a point with a larger distance value may be nearer to the center of the blood vessel than a point with a smaller distance value.

In step 830, the centerline of the blood vessel in the image to be processed may be adjusted based on the distance field. The adjustment operation may correct the extracted centerline of the blood vessel. In some embodiments, for the distance field obtained in step 828, a feature point with a distance value closer to priori information (e.g., the radius of the blood vessel) may be assigned with a higher weight value. For example, if the radius of the blood vessel is 5 mm, then the distance field value of the centerline of the blood vessel may be from 5 to 10 mm (D to 2D, D is the radius of the blood vessel). The points satisfying the distance field value may be assigned with a high weight value, and other points may be assigned with a low weight value. The weight value herein may be default settings of the system, or may be set by a user. The centerline average model may be adjusted by using the weight values and the constraints of shape parameters in the ASM algorithm, and the centerline of the blood vessel obtained by mapping may continuously be moved away from the distance boundary to converge to the center of the blood vessel. In some embodiments, the blood vessel may be extracted according to the adjusted centerline of the blood vessel.

It should be noted that, in some situations, the weight values cannot be directly determined according to the radius of the blood vessel. For example, in a head area, the blood vessel is close to the bone. In this situation, a point with a distance field value satisfying 2D may be at the boundary between the blood vessel and the bone, then the weight value should be adjusted according to the particular case.

Figure 9:
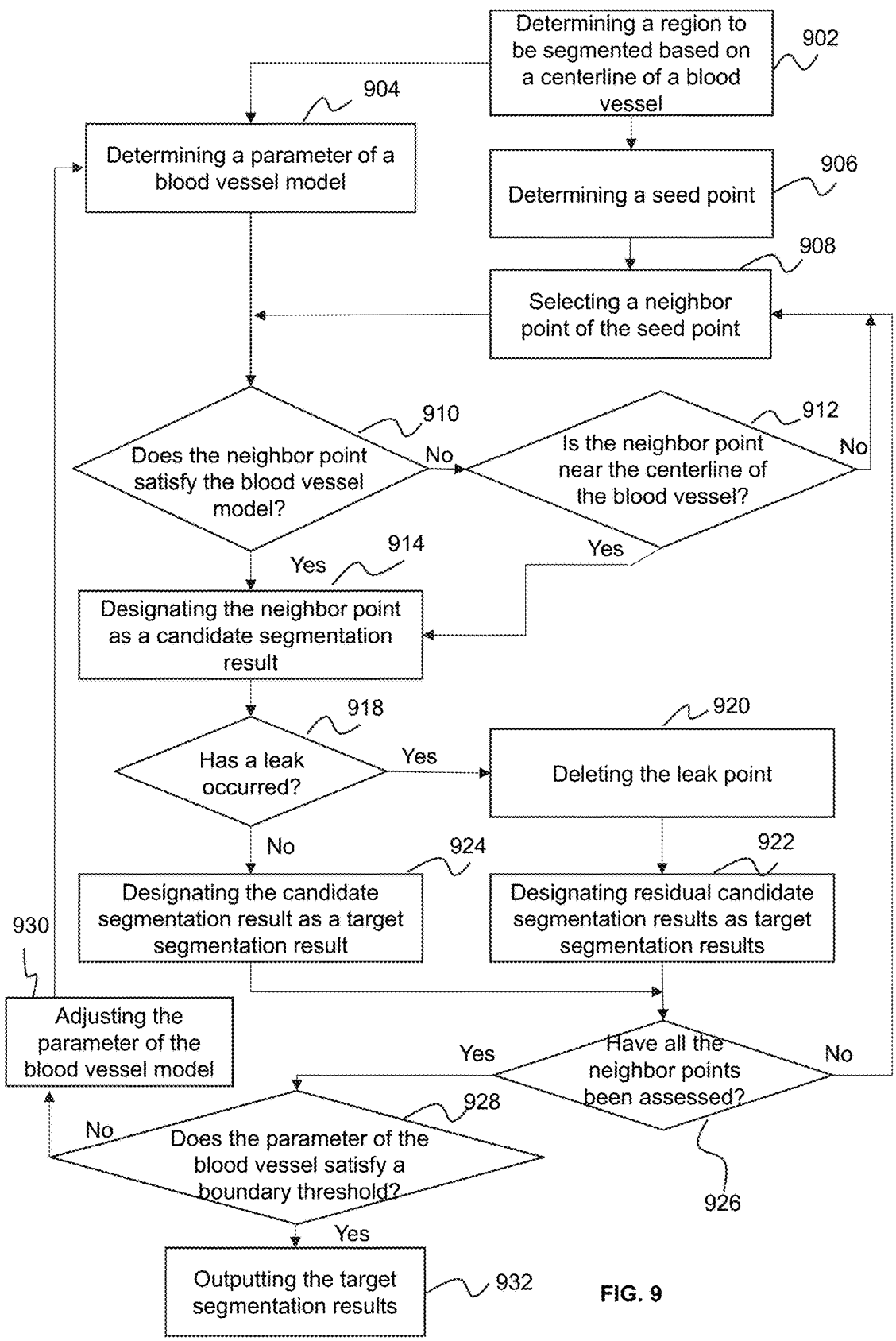
FIG. 9 is a flowchart illustrating an exemplary process for extracting a blood vessel based on a centerline of the blood vessel according to some embodiments of the present disclosure.

FIG. 9 is a flowchart illustrating an exemplary process for extracting a blood vessel based on a centerline of the blood vessel according to some embodiments of the present disclosure. In some embodiments, the process for extracting a blood vessel may be performed by the extraction sub-unit 520. In step 902, a region to be segmented may be determined based on a centerline of a blood vessel. In some embodiments, taking the centerline as a center, a certain region may be selected from the center to determine the region to be segmented. In some embodiments, the region to be segmented may be set according to the size of the blood vessel. For example, a region centered with the centerline and with a radius of 15 mm may be set as the region to be segmented.

In step 904, a parameter of a blood vessel model may be determined. The parameter of the blood vessel model may include a radius, a direction, a boundary condition, a boundary gradient, a boundary gray value, an enhanced condition, etc. In some embodiments, the parameter of the blood vessel model may be default settings of the system, or may be set by a user. In step 906, a seed point may be determined. In some embodiments, any point in the region to be segmented may be selected as the seed point. In step 908, a neighbor point of the seed point may be selected. The neighbor point herein may refer to a pixel within a certain range of the seed point. For example, several points (e.g., 6 points, 26 points, etc.) above, below, on left of, on right of, in front of, and behind the seed point may be selected as neighbor points.

In step 910, whether the neighbor point satisfies the parameter of the blood vessel model may be determined. In some embodiments, whether image features of the neighbor point satisfy the parameter of the blood vessel model may be determined. In some embodiments, the image features may correspond to multiple feature images. The feature images herein may include a Laplacian image, a gradient image, a maximum value rate image, etc. The image features may include a gray value, a gradient value, a Laplacian value, a maximum value rate, etc.

In some embodiments, the process in which whether the image features satisfy the parameter of the current blood vessel model may be determined may include: if the neighbor point has a gradient smaller than the boundary gradient, a maximum value rate greater than the boundary maximum value rate, a Laplacian value between the boundary Laplacian values, and the gray value between the boundary gray conditions, the neighbor point may be determined as satisfying the parameter of the blood vessel model; otherwise, the neighbor point may be determined as not satisfying the parameter of the blood vessel model.

If the neighbor point satisfies the parameter of the blood vessel model, the neighbor point may be determined as a candidate segmentation result in step 914. If the neighbor point does not satisfy the parameter of the blood vessel model, the neighbor point may be further determined that whether it is near the center of the blood vessel in step 912. If the neighbor point is not near the center of the blood vessel, the neighbor point may be abandoned, and the process may return to step 908 to re-select other neighbor points. If the neighbor point is near the center of the blood vessel, the neighbor point may be determined as a candidate segmentation result in step 914. In some embodiments, whether the neighbor point is near the center of the blood vessel may be determined based on a center condition. The center condition herein may refer to that whether an image feature of a point is near the image feature of the center of the blood vessel may be determined. In some embodiments, whether the neighbor point is near the center of the blood vessel may be determined based on a gradient value, a Laplacian value, a maximum value rate, etc. For example, if a maximum value rate of the neighbor point is greater than the maximum value rate of a point far away from the center of the blood vessel, or a gradient value of the neighbor point is smaller than the gradient value of a point far away from the center, the neighbor point may be determined to be near the center of the blood vessel. In some embodiments, the distance from a neighbor point to the center of the blood vessel may be compared with the distance from a seed point to the center of the blood vessel. For example, if a neighbor point is nearer the center of the blood vessel than the seed point, the neighbor point may be determined as satisfying the center condition.

In step 918, whether a leak has occurred may be determined after the candidate segmentation result is determined in step 914. The leak herein may refer to that the candidate segmentation result may include some points not satisfying the parameter of the current model. In some embodiments, whether a leak has occurred may be determined based on a global condition. In some embodiments, a global condition threshold may be set. The global condition threshold may be default settings of the system, or may be set by a user. For example, if the blood vessel is a tube structure, the amount of points that may be expanded outward along the current candidate segmentation result may satisfy a certain threshold condition. The threshold condition may be set as the global condition threshold. In some embodiments, whether the leak has occurred may be determined by comparing the amount of the current candidate segmentation result with the global condition threshold. For example, if the amount of the current candidate segmentation result is far less than the global condition threshold, a leak may have occurred, and then the leak point may be deleted in step 920. Further, in step 922, the residual candidate segmentation result may be designated as the target candidate segmentation result. If the amount of the current candidate segmentation result is greater than the global condition threshold, it may be determined that the global condition is satisfied. In step 924, the candidate segmentation result may be designated as the target candidate segmentation result.

In step 926, whether all the neighbor points have been assessed may be determined after the target candidate segmentation result is determined. If not all the neighbor points have been assessed, the process may return to step 908 to select one or more other neighbor points to assess. If all the neighbor points have been assessed, step 928 may be performed to further determine whether the parameter of the blood vessel model satisfies a boundary threshold. In step 928, the boundary threshold may be default settings of the system, or may be set by a user. For example, a blood vessel may be divided into three portions from inside to outside including: an inner circle structure located at the center of the blood vessel, a middle ring structure close to the inner circle, and an outermost ring structure wrapping the blood vessel. The boundary threshold may refer to the model boundary parameter at the outermost ring structure.

If the parameter of the blood vessel model satisfies the boundary threshold, the target segmentation result may be output in step 932. If the parameter of the blood vessel model does not satisfy the boundary threshold, the parameter of the model may be adjusted in step 930. In some embodiments, the model boundary parameter may be extended one or more times. For example, the model boundary parameter may be adjusted as a model parameter of the inner circle structure. Further, the model boundary parameter may be adjusted as a model parameter of the inner ring of the middle ring structure. Furthermore, the model boundary parameter may be adjusted as a model parameter of the inner ring of the middle ring structure.

In some embodiments, the blood vessel may be segmented according to the target segmentation result. In some embodiments, whether the blood vessel has been segmented successfully may be further determined. If the blood vessel were not segmented successfully, the blood vessel may be re-segmented based on other segmentation techniques until the segmentation is successfully performed. For example, the blood vessel may be divided into different regions to guarantee that there is only one complete main blood vessel in one region. Further, the main blood vessel in each of the regions may be segmented for determining whether the blood vessel is segmented successfully. In some embodiments, the main blood vessel in different regions may be segmented based on different segmentation technique. For example, the aneurysmal blood vessel may be segmented according to gray values and gradient values of an image. The internal carotid may be segmented based on a shape constraint technique. Further, if the blood vessel is not segmented successfully, other alternative segmentation techniques may be selected by using an iterator pattern until the segmentation is successfully performed. In some embodiments, the alternative segmentation techniques may include a pattern recognition method, a model-based method, a tracking-based method, an artificial intelligence method, a neural network method, a tubular object detection method, etc.

Figure 10:
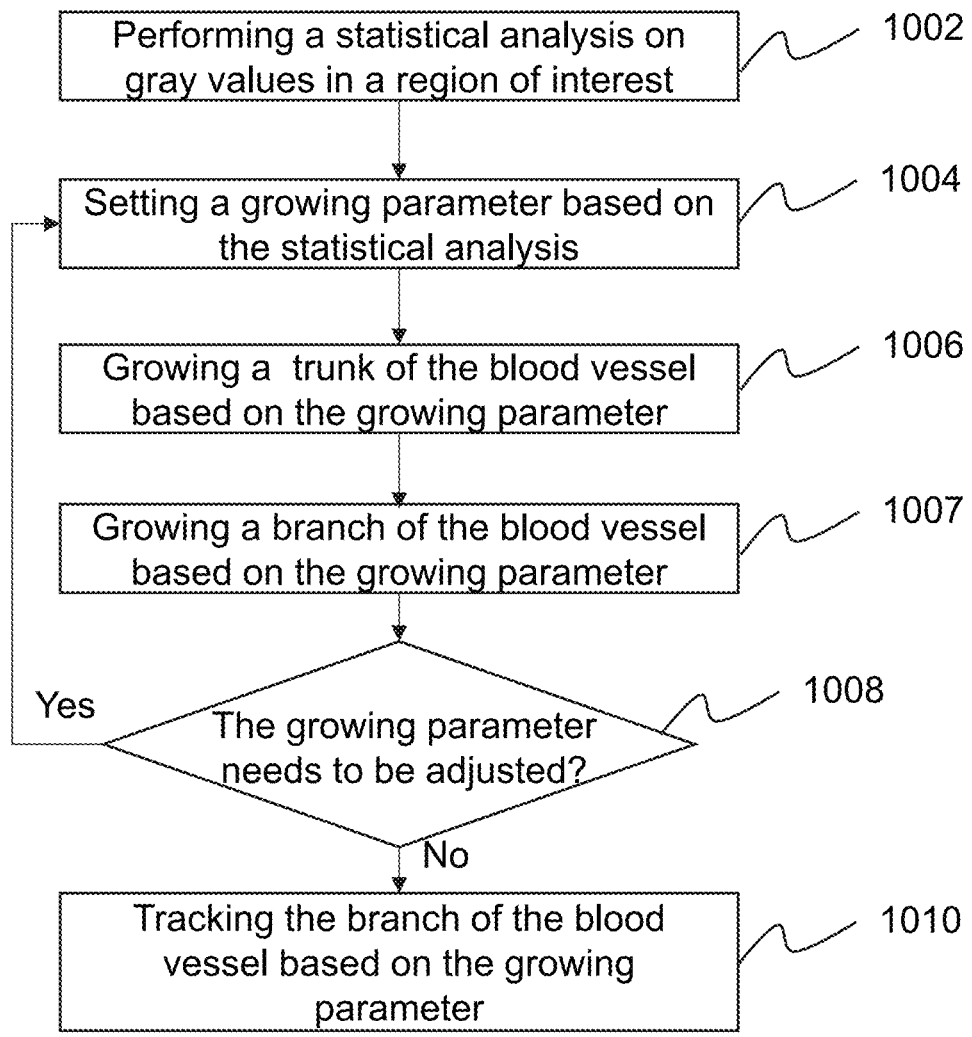
FIG. 10 is a flowchart illustrating an exemplary process for extracting a blood vessel according to some embodiments of the present disclosure.

FIG. 10 is a flowchart illustrating an exemplary process for extracting a blood vessel according to some embodiments of the present disclosure. The process for extracting a blood vessel may be performed by the extraction sub-unit 520. It should be noted that FIG. 10 is an exemplary process and it does not mean that the present disclosure must be carried out in accordance with the following operations. In some embodiments, one or more operations may be deleted or the order may be adjusted. As shown in FIG. 5-B, an ROI may be determined before the blood vessel is extracted. In some embodiments, the ROI may include a head, a cervix, an abdomen, a lower limb, etc. For example, a liver region may be determined before extracting the blood vessel of the abdomen (e.g., a hepatic portal vein). In some embodiments, a position where a portal vein enters the liver layers may be determined roughly according to the anatomy information of the liver. For example, the position where the portal vein enters the liver layers may be estimated according to the change of the liver area in each layer. In some embodiments, the position where the portal vein enters the liver layer may be determined based on a local Hessian enhancement. In some embodiments, a seed point of the blood vessel may be positioned on the position where the portal vein enters the liver layers.

In step 1002, a statistical analysis may be performed on gray values in a region of interest (ROI). In some embodiments, the statistical analyses may be performed on gray values of the liver and gray values of the blood vessel. In some embodiments, a gray image may be determined and the statistical analysis may be performed on gray values of the gray image. In step 1004, a growing parameter may be set based on the statistical analysis. In some embodiments, the growing parameter may relate to a growth algorithm. The growth algorithm may include a fast marching algorithm. The growing parameter may include a gray threshold, an iteration number, a growing range of the blood vessel, etc. In step 1006, a trunk of the blood vessel may be grown based on the growing parameter by performing the growth algorithm. In step 1007, a branch of the blood vessel may be further grown based on the growing parameter.

In step 1008, whether the growing parameter needs to be adjusted may be determined. In some embodiments, step 1008 may be performed in real time, or may be performed in a certain time interval. In some embodiments, whether the growing parameter needs to be adjusted may be determined according to the flow of a blood vessel contrast and/or the state of the current blood vessel region. If needed, the process may return to step 1004 to adjust the growing parameter (e.g., a gray threshold, an iteration number, etc.). The trunk and/or the branch of the blood vessel may be further grown according to the adjusted growing parameter in step 1006 and/or step 1007. If not needed, the branch of the blood vessel may be tracked based on the growing parameter (e.g., in the growing range of the blood vessel) in step 1010.

Figure 11:
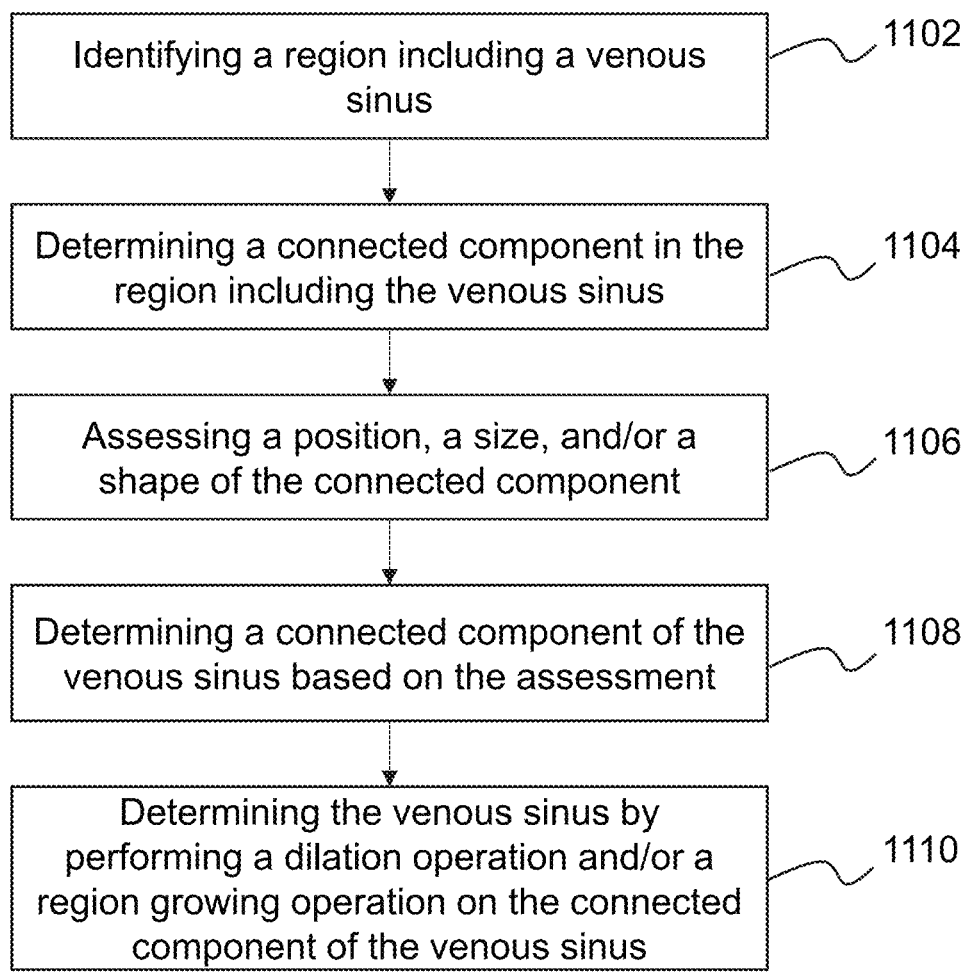
FIG. 11 is a flowchart illustrating an exemplary process for extracting a specific portion of a blood vessel according to some embodiments of the present disclosure.

FIG. 11 is a flowchart illustrating an exemplary process for extracting a specific portion of a blood vessel according to some embodiments of the present disclosure. In some embodiments, a specific portion of a blood vessel may be extracted according to the segmented (or extracted) blood vessel. For example, a venous sinus may be extracted from the extracted blood vessel. In some embodiments, the process for extracting the venous sinus may be performed by the feature extraction sub-unit 530. In step 1102, a region including a venous sinus may be determined. In some embodiments, the region including the venous sinus may be a strip region. In some embodiments, the region including the venous sinus may be determined based on the extracted blood vessel. The blood vessel may be extracted as described elsewhere in the disclosure. In some embodiments, the region including the venous sinus may be determined by a combination of a core dilation and a core erosion. Specifically, mask images may be obtained respectively by performing the core dilation and the core erosion. And the region including the venous sinus may be determined based on the mask images. The mask images herein may refer to that a specific part of an image may be blocked or covered and then the specific part of the image may be highlighted. For example, a mask 1 may be obtained by performing a core dilation with a 10 mm width on a cerebrum region, and a mask 2 may be obtained by performing a core erosion with a 20 mm width on the cerebrum region. The marked regions in the mask 1 and mask 2 may be subtracted to obtain the strip region including the venous sinus.

In step 1104, a connected component in the region may be determined. The connected component herein may refer to an image region including pixels with same pixel values and being adjacent with each other in the region. In some embodiments, the connected component in the region including the venous sinus may be obtained based on an erosion operation. For example, an erosion operation may be performed on masks of the blood vessel in the region including the venous sinus to obtain different connected components.

In step 1106, positions, sizes and/or shapes of the connected components may be assessed. In some embodiments, the position of each connected component may be assessed. Whether a connected component is a connected component of the venous sinus may be determined according to the position of each connected component. For example, if a connected component is located in front and bottom of the brain, the connected component may be determined to be an arterial puncture area, and not the connected component of the venous sinus. In some embodiments, the sizes and/or shapes of the connected components may be assessed. Whether a connected component is the connected component of the venous sinus may be assessed according to the size and/or the shape of each connected component. In some embodiments, in order to determine whether a connected component is the connected component of the venous sinus, a threshold may be set. The threshold herein may be default settings of the system, or may be set by a user. In some embodiments, different subjects may correspond to different thresholds. In some embodiments, one or more thresholds may be set. For example, a first volume threshold, a second volume threshold, and a third volume threshold, etc., may be set. In some embodiments, the first threshold, the second threshold, and/or the third threshold may decrease successively. For example, because a space size of the venous sinus region is large, if a volume of a connected component is greater than the first threshold, the connected component may be determined to be the connected component of the venous sinus. Further, because the space size of the venous sinus region is similar to a space size of a cerebral artery, and a shape of the venous sinus region is elongate, if a volume of a connected component is greater than the second threshold and a shape of the connected component is elongate, the connected component may be determined to be the connected component of the venous sinus. Further, because a space volume of the terminal region of the venous sinus is relatively small and the terminal region is generally located at the top of the cerebrum region, if a volume of a connected component is volume greater than the third threshold and the connected component is located at the top of the cerebrum region, the connected component may be determined to be the connected component of the venous sinus.

Whether a connected component is the connected component of the venous sinus may be determined by comparing the volume of the connected component with the above thresholds. For example, if a volume of a connected component is greater than the first threshold, the connected component may be determined to be the connected component of the venous sinus. As another example, if a volume of a connected component is greater than the second threshold and a shape of the connected component is elongate, the connected component may be determined to be the connected component of the venous sinus. As a further example, if a volume of a connected component is volume greater than the third threshold and the connected component is located at the top of the cerebrum region, the connected component may be determined to be the connected component of the venous sinus.

In step 1108, a connected component of the venous sinus may be determined based on the assessment. In some embodiments, the connected component of the venous sinus may be marked for further process. In step 1110, a dilation operation and/or a region growing operation may be performed on the connected component of the venous sinus to obtain a venous sinus. For example, the dilation operation may be performed on the connected component of the venous sinus by performing a core dilation to obtain a preliminary venous sinus. Further, taking the preliminary venous sinus as a starting region, the region growing operation may be performed to obtain a complete venous sinus. In some embodiments, the direction of the region growing may be from a cerebrum core to the strip region of the venous sinus.

Figure 12:
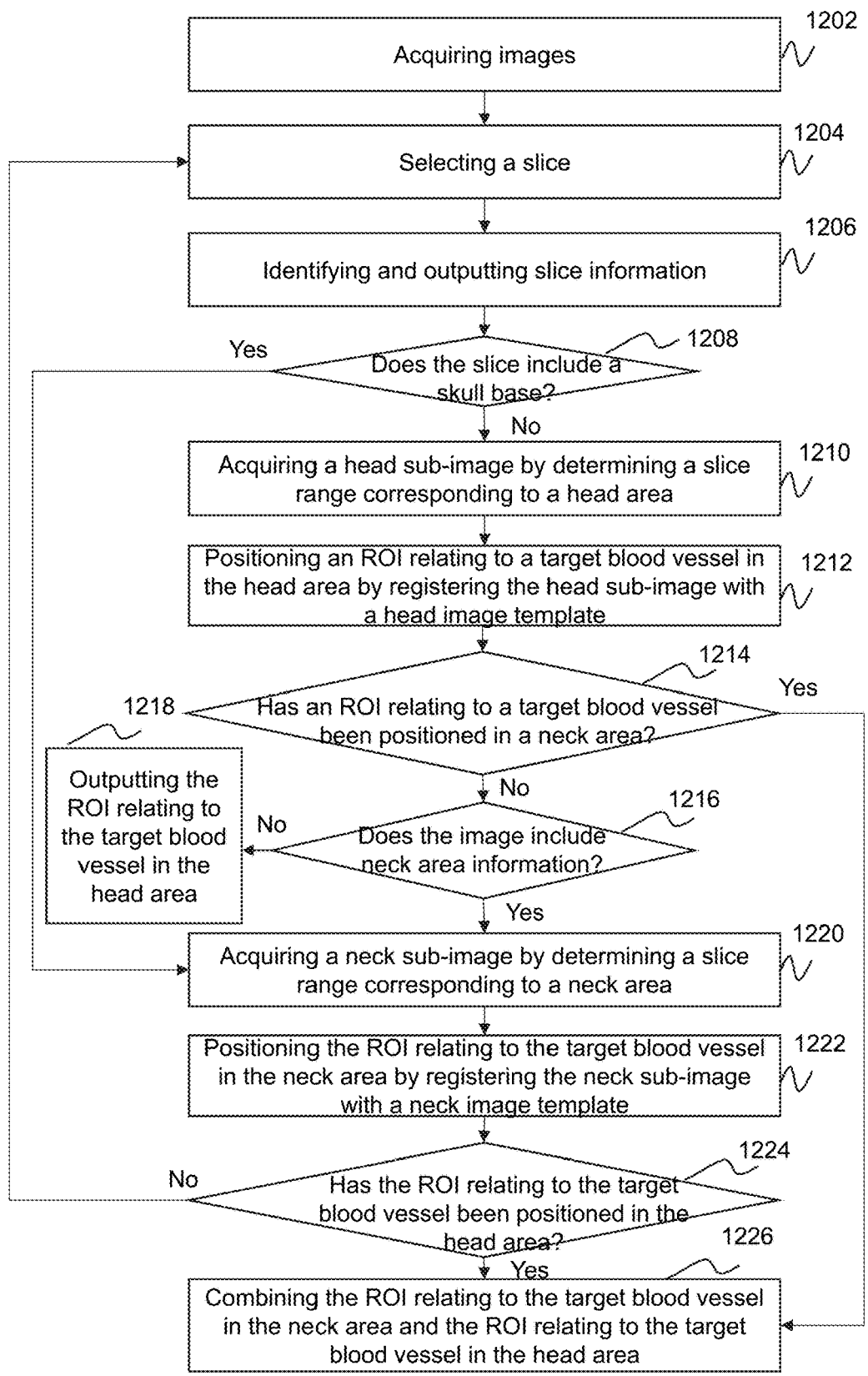
FIG. 12 is a flowchart illustrating an exemplary process for determining a region of interest (ROI) in a head-neck area according to some embodiments of the present disclosure.

FIG. 12 is a flowchart illustrating an exemplary process for determining a region of interest (ROI) in a head-neck area according to some embodiments of the present disclosure. The ROI relating to a target blood vessel in a head-neck area determined according to the process illustrated in FIG.

12 may be found in FIGS. 13-A through 13-M. In step 1202, images may be acquired. In some embodiments, the images may include head information and neck information. In step 1204, a slice may be selected.

In step 1206, slice information may be identified and outputted. In some embodiments, the slice information may be identified based on a shape of a slice and a size of the slice. For example, the maximum values of an outline (e.g., a head outline) in the image in the horizontal direction and in vertical direction may be determined and the determination result may be compared with a preset threshold to identify the slice information. In some embodiments, one or more preset thresholds may be set. For example, a first threshold a1 and a second threshold a2 may be set. The thresholds may be default settings of the system, or may be set by a user. If the determination result is not less than the threshold a1, the slice may be determined to be a half head; if the determination result is smaller than the threshold a2, the slice may be determined to be a blank slice or a vertex. In some embodiments, if the determination result does not satisfy the above conditions, several slices may be captured from the selected slice to acquire a maximum density projection image of the several slices. Further, the selected slice may be determined to be a skull base or a full head according to the number of connected components in the maximum density projection image. In some embodiments, a maximum density projection may be performed on a binary image of the several slices to obtain a maximum density projection image. In some embodiments, the binary image may be obtained by performing a binarization operation on the selected several slice based on a bone threshold.

In step 1208, whether the selected slice include a skull base may be determined according to the slice information. If the selected slice includes a skull base, the process may proceed to step 1220 to determine a slice range of a neck area and obtain a neck sub-image. If the selected slice does not include a skull base, the process may proceed to step 1210 to determine a slice range of a head area and obtain a head sub-image. In some embodiments, region sub-images may be dynamically divided according to the position information of the slices. For example, if the selected slice does not include the skull base, the slice range of the head area may be determined based on the position information of the selected slice and anatomical features, such as a head height, a position of foramen magnum, an atlas position, etc., or a skull segmentation method may be used to determine the slice range, and the head sub-image may be extracted from the image.

In step 1212, the head sub-image may be registered with a head image template to position an ROI relating to a target blood vessel in the head area. In some embodiments, an affine registration may be performed on the head sub-image and the head image template to position the ROI relating to the target blood vessel in the head area. The head image template may be a standardized image template. In some embodiments, anatomical structural features may be used to assist the affine registration. For example, if the target blood vessel is a transcranial segment of a vertebral artery and/or a basilar artery, a position of the foramen magnum may be identified in the head sub-image and the head image template to be as a feature of the affine registration to assist the registration process. As another example, if the target blood vessel is an internal carotid, a cavernous sinus, a sphenoid, a sphenoid sinus, etc., may be identified to be as the feature of the affine registration to assist the registration process.

In step 1214, whether an ROI relating to a target blood vessel in a neck area has been positioned may be determined. If the ROI relating to the target blood vessel in the neck area has been positioned, the process may proceed to step 1226, the ROI relating to the target blood vessel in the neck area and the ROI relating to the target blood vessel in the head area may be combined to obtain an ROI relating to a target blood vessel in the head-neck area. If the ROI relating to the target blood vessel in the neck area has not been positioned, the process may proceed to step 1216 to determine whether the image include neck area information. If the image does not include neck area information, the process may proceed to step 1218 to directly output the ROI relating to the target blood vessel in the head area. If the image includes neck area information, the process may proceed to step 1220 to determine a slice range of the neck area and obtain a neck sub-image. In some embodiments, the slice range of the neck area may be determined according to anatomical features, such as a cervical vertebra height, a vertebra position, etc., and the neck sub-image may be captured from the image.

In step 1222, the neck sub-image may be registered with a neck image template to position the ROI relating to the target blood vessel in the neck area. The neck image template may be a standardized image template. In some embodiments, anatomical structural features may be used to assist the affine registration. For example, if the target blood vessel is a vertebra penetrating segment of a vertebral artery, a position of the neck vertebra in the neck sub-image and the neck image template may be identified to be as a feature of the affine registration to assist the registration process.

In step 1224, whether the ROI relating to the target blood vessel in the head area has been positioned may be determined. If the ROI relating to the target blood vessel in the head area has been positioned, the process may proceed to step 1226, the ROI relating to the target blood vessel in the neck area and the ROI relating to the target blood vessel in the head area may be combined to obtain an ROI of the target blood vessel in the head-neck area. If the ROI relating to the target blood vessel in the head area has not been positioned, the process may return to step 1204 to select other slices to be further assessed.

FIGS. 13-A through 13-F illustrate a group of exemplary experimental result images for determining a region of interest (ROI) relating to a target blood vessel in a head-neck area according to some embodiments of the present disclosure. The target blood vessel in the head-neck area may include a transcranial segment blood vessel of the internal carotid, a transcranial segment blood vessel of the vertebral artery, a vertebra penetrating segment blood vessel of the vertebral artery, and a basilar artery. FIG. 13-A shows an image illustrating a positioning effect of the ROIs of the transcranial segment blood vessel of the internal carotid. The regions $A_1$, $A_2$, and $A_3$ represent masks of the ROIs of the transcranial segment blood vessel of the internal carotid. FIG. 13-B shows an image illustrating a positioning effect of the ROIs of the transcranial segment blood vessel of the vertebral artery. The regions $B_1$, $B_2$, and $B_3$ represent masks of the ROIs of the transcranial segment blood vessel of the vertebral artery. FIG. 13-C shows an image illustrating a positioning effect of the ROI of the vertebra penetrating segment blood vessel of the vertebral artery. The region in the frame represents a mask of the ROI of the vertebra penetrating segment blood vessel of the vertebral artery. FIG. 13-D shows an image illustrating a positioning effect of the ROI of the basilar artery. The region in the frame represents a mask of the ROI of the basilar artery. FIG. 13-E shows a three-dimensional image of the ROI of the target blood vessel (right/left) (as shown by $E_1$, $E_2$, and $E_3$ in FIG.

13-E). FIG. 13-F shows a three-dimensional image of the ROI of the target blood vessel (left/right) (as shown by $F_1$, $F_2$, and $F_3$ in FIG. 13-F).

FIGS. 13-G through 13-M illustrate another group of exemplary experimental result images for determining a region of interest (ROI) relating to a target blood vessel in a head-neck area according to some embodiments of the present disclosure. The target blood vessel in the head-neck area may include a transcranial segment blood vessel of the internal carotid, a transcranial segment blood vessel of the vertebral artery, a vertebra penetrating segment blood vessel of the vertebral artery, and a basilar artery. FIG. 13-G shows an image illustrating a positioning effect of the ROIs of the transcranial segment blood vessel of the internal carotid. The regions $G_1$ and $G_2$ represent masks of the ROIs of the transcranial segment blood vessel of the internal carotid. FIG. 13-H shows an image illustrating a positioning effect of the ROIs of the transcranial segment blood vessel of the vertebral artery. The regions $H_1$ and $H_2$ represent masks of the ROIs of the transcranial segment blood vessel of the vertebral artery. FIGS. 13-I and 13-J show images illustrating a positioning effect of the ROIs of the vertebra penetrating segment blood vessel of the vertebral artery. The region in the frame represents a mask of the ROI of the vertebra penetrating segment blood vessel of the vertebral artery. FIG. 13-K shows an image illustrating a positioning effect of the ROI of the basilar artery. The region in the frame represents a mask of the ROI of the basilar artery. FIG. 13-L shows an image in which the ROIs of the target blood vessel has been determined (as shown by I, II, III, IV, and V in FIG. 13-L). FIG. 13-M shows a three-dimensional image of the ROIs in the target blood vessel (left/right) (as shown by I, II, III, IV, and V in FIG. 13-M).

FIGS. 14-A and 14-B illustrate exemplary experimental result images for determining a centerline of a blood vessel based on a training according to some embodiments of the present application. As shown in FIGS. 14-A and 14-B, an enhanced image of a blood vessel was obtained based on a strong classifier. The arrows indicate blood vessel regions. The left image of FIG. 14-A is an initial registration image and the right image is an enhanced image of a vertebral artery blood vessel. The left image of FIG. 14-B is an initial registration image and the right image is an enhanced image of the vertebral artery blood vessel. As shown in the figures, since the accuracy of classification was increased, the contrast between the blood vessel and the around tissues was obviously improved.

FIGS. 15-A through 15-D illustrate a first group of exemplary experimental result images for extracting a blood vessel based on a centerline of the blood vessel according to some embodiments of the present disclosure. FIG. 15-A shows a cross-sectional image of a segmentation result of a carotid artery. FIG. 15-B shows a sagittal image. FIG. 15-C shows a three-dimensional image. FIG. 15-D shows a coronal image.

FIGS. 15-E through 15-H illustrate a second group of exemplary experimental result images for extracting a blood vessel based on a centerline of the blood vessel according to some embodiments of the present disclosure. Similarly, the four images show a cross-sectional image, a sagittal image, a three-dimensional image, and a coronal image of the segmentation result of the carotid artery, respectively. FIGS. 15-I through 15-L illustrate a third group of experimental result images for extracting a blood vessel based on a centerline of a blood vessel according to some embodiments of the present disclosure. Similarly, the four images show a cross-sectional image, a sagittal image, a three-dimensional image, and a coronal image of the segmentation result of the carotid artery, respectively. FIGS. 15-M through 15-P illustrate a fourth group of experimental result images for extracting a blood vessel based on a centerline of a blood vessel according to some embodiments of the present disclosure. Similarly, the four images show a cross-sectional image, a sagittal image, a three-dimensional image, and a coronal image of the segmentation result of the carotid artery, respectively.

FIGS. 16-A through 16-G illustrate exemplary experimental result images for extracting a hepatic portal vein according to some embodiments of the present disclosure. As shown in FIG. 16-A, a liver region was firstly segmented, a sagittal image of the liver region is shown in the figure. Then, an approximate position where the portal vein enters the liver was estimated according to the area change of the liver in each layer. FIG. 16-B shows a cross-sectional image of the position where the portal vein enters the liver region. After the position where the portal vein enters the liver region was determined, a Hessian enhancement was performed on the regions near the portal vein, and an enhanced image was obtained as shown in FIG. 16-C. In the enhanced image, a position of a blood vessel of the portal vein in the position where the portal vein enters the liver was determined and a seed point of the blood vessel was positioned in the position. Then, a gray value range of the liver and gray values of the blood vessel of the portal vein were determined. A threshold of the blood vessel of the portal vein was estimated based on a Gaussian curve fitting algorithm. Then, the blood vessel was grown based on the fast marching algorithm, as shown in FIGS. 16-D and 16-E, a trunk of the portal vein was extracted. Then, a trunk center of the hepatic portal vein was positioned based on a relationship between the liver and the portal vein. As shown in FIGS. 16-F and 16-G, taking the trunk center of the hepatic portal vein as a starting point, branches of the portal vein were extracted based on the trunk of the portal vein.

FIG. 17 is an exemplary image of a U field according to some embodiments of the present disclosure. The determination of the U values may be found in step 812 and the description thereof.

The above descriptions may disclose different aspects of methods for extracting a blood vessel and/or methods for implanting other operations by procedures. The procedures in the disclosure may be considered as "product" or "merchandise" existing in the form of executable codes and/or related data, which may be participated or implemented by a computer readable medium. A tangible and permanent storage medium may include any memory or storage used by a computer, a processor, a similar device, or a related module, for example, a semiconductor memory, a tape drive, a disk drive, or other devices that may provide storage functions for software at any time.

All software or a part of it may communicate over a network, such as the Internet or other communication networks. Such communications may load software from one computer device or processor to another. For example: from a management server or host computer in an on-demand service system loaded to a computer hardware platform, or other computer environment, or the similar function system relating to provide information required by the on-demand services. Thus, another medium that may deliver software elements may also be used as physical connections between local devices, such as light waves, radio waves, electromagnetic waves, etc., through cables, cables, or air. A physical medium used for a carrier, such as a cable, a wireless connection, or an optical cable, may also be considered a medium for carrying software. Here, unless the physical storage medium is restricted, other terms that may represent the computer or machine "readable medium" represent the medium in which a processor executes any instruction.

Therefore, a computer readable medium may have many forms, including, a visible storage media, a carrier media, or a physical transmission media. Stable storage media may include compact disks (CD), disks, or storage systems used in other computers or similar devices that may enable the system components described in the diagrams. Unstable storage media may include a dynamic memory, such as the main memory of a computer platform. The tangible transmission medium may include a coaxial cable, a copper cable, an optical fiber, and a circuitry forming the bus within the computer system. A carrier transmission medium may transmit electrical signals, electromagnetic signals, acoustic signals, or light wave signals, which may be generated by radio frequency or infrared data communication. A computer readable medium may include a hard disk, a floppy disk, a magnetic tape, any other magnetic medium; a CD-ROM, a DVD, a DVD-ROM, any other optical media; a hole punched card, and any other physical storage medium containing a hole patterns; an RAM, a PROM, an EPROM, a FLASH-EPROM, or any other memory chip tape; a carrier for data or instructions transmission, cable, a connection device for carrier transmission, or any other computer that may be used to read the code and/or data. In the form of these computer readable media, there are a variety of processes that occur when the processor is executing instructions and delivering one or more results Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python, etc., conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

The contents disclosed in this application can be diversified and improved. For example, different system components described above may be implemented by hardware, or software. For example, the system may be installed on the existing server. In addition, the location information disclosed here may be implemented through a firmware, a combination of firmware and software, a combination of firmware and hardware, or a combination of hardware, firmware and software.

The above descriptions may describe this application and/or some other examples. According to the above contents, the application may also make different variations. The topics disclosed in this application may be implemented in different forms and examples, and this application may be applied to a large number of applications. All the applications, modifications and changes required in the post claims are within the scope of this application.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment," "one embodiment," or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A method for extracting a blood vessel implemented on at least one machine each of which has at least one processor and storage, the method comprising:
    acquiring an image relating to a blood vessel, the image including multiple slices;
    determining a region of interest in the image;
    determining a centerline of the blood vessel;
    establishing a blood vessel model; and
    extracting the blood vessel from the region of interest based on the blood vessel model and the centerline of the blood vessel,
    wherein the centerline of the blood vessel is determined according to one or more operations including:
        retrieving training samples;
        performing a classifier training based on the training samples to determine weak classifiers;
        combining the weak classifiers to determine a strong classifier;
        determining an enhanced image based on the strong classifier; and
        determining the centerline of the blood vessel in the enhanced image based on a fast marching algorithm.

2. The method of claim 1, wherein the determining a region of interest in the image comprises:
    identifying slice information relating to the multiple slices of the image;
    determining a slice range of the multiple slices corresponding to a sub-image based on the slice information;
    determining the sub-image in the slice range;
    acquiring a template based on the sub-image;
    registering the sub-image based on the template to determine a registered result; and
    identifying the region of interest based on the registered result.

3. The method of claim 1, wherein the determining a region of interest in the image comprises performing machine learning.

4. The method of claim 1, further comprising determining a seed point of the blood vessel including:
    performing an enhancement operation on the image to obtain a second enhanced image;
    determining gradients of grey values relating to the image to obtain a gradient image;
    constructing a feature function of the blood vessel based on the second enhanced image and the gradient image; and
    determining the seed point of the blood vessel based on the feature function of the blood vessel.

5. The method of claim 1, wherein the training samples include a positive training sample and a negative training sample.

6. The method of claim 1, the extracting the blood vessel based on the blood vessel model and the centerline of the blood vessel including:
    determining a first segmentation result based on the centerline of the blood vessel;
    determining a second segmentation result based on the first segmentation result;
    assessing the second segmentation result based on a global condition to determine a third segmentation result;
    determining a boundary condition relating to the blood vessel model;
    assessing the third segmentation result based on the boundary condition to determine a fourth segmentation result; and
    extracting the blood vessel based on the fourth segmentation result.

7. The method of claim 1, wherein the blood vessel is extracted by a segmentation technique relating to an aneurysmal blood vessel, a segmentation technique relating to a blood vessel with a low dose contrast agent, or a segmentation technique relating to a calcific malformation blood vessel.

8. The method of claim 1, wherein the extracting the blood vessel comprises:
    performing a statistical analysis on gray values within the region of interest;
    determining a growing parameter based on the statistical analysis;
    determining a trunk of the blood vessel based on a fast marching algorithm; and
    tracking a branch of the blood vessel by adjusting the growing parameter.

9. The method of claim 1, further comprising extracting a specific portion of the blood vessel including:
    determining a region including the specific portion of the blood vessel;
    determining a first connected component in the region;
    extracting a feature of the first connected component;
    determining a connected component of the specific portion based on the feature of the first connected component; and
    determining the specific portion of the blood vessel based on the connected component of the specific portion.

10. The method of claim 9, wherein the feature of the first connected component includes a position, a size, or a shape of the first connected component.

11. The method of claim 9, wherein the determining the specific portion of the blood vessel comprises performing a dilation operation or a region growing operation on the determined connected component of the specific portion.

12. A system for extracting a blood vessel, the system comprising:
    at least one processor; and
    executable instructions, the executable instructions being executed by the at least one processor, causing the at least one processor to implement a method, comprising:
        acquiring an image relating to a blood vessel, the image including multiple slices;
        determining a region of interest in the image;
        determining a centerline of the blood vessel;

establishing a blood vessel model; and
extracting the blood vessel from the region of interest based on the blood vessel model and the centerline of the blood vessel,
wherein the centerline of the blood vessel is determined according to one or more operations including:
retrieving training samples;
performing a classifier training based on the training samples to determine weak classifiers;
combining the weak classifiers to determine a strong classifier;
determining an enhanced image based on the strong classifier; and
determining the centerline of the blood vessel in the enhanced image based on a fast marching algorithm.

13. The system of claim 12, wherein the determining a region of interest in the image comprises:
identifying slice information relating to the slices of the image;
determining a slice range of the multiple slices corresponding to a sub-image based on the slice information;
determining the sub-image in the slice range;
acquiring a template based on the sub-image;
registering the sub-image based on the template to determine a registered result; and
identifying the region of interest based on the registered result.

14. The system of claim 12, further comprising determining a seed point of the blood vessel including:
performing an enhancement operation on the image to obtain a second enhanced image;
determining gradients of grey values relating to the image to obtain a gradient image;
constructing a feature function of the blood vessel based on the second enhanced image and the gradient image; and
determining the seed point of the blood vessel based on the feature function of the blood vessel.

15. A non-transitory computer readable medium, comprising:
instructions being executed by at least one processor, causing the at least one processor to implement a method, comprising:
acquiring an image relating to a blood vessel, the image including multiple slices;
determining a region of interest in the image;
determining a centerline of the blood vessel;
establishing a blood vessel model; and
extracting the blood vessel from the region of interest based on the blood vessel model and the centerline of the blood vessel,
wherein the centerline of the blood vessel is determined according to one or more operations including:
retrieving training samples;
performing a classifier training based on the training samples to determine weak classifiers;
combining the weak classifiers to determine a strong classifier;
determining an enhanced image based on the strong classifier; and
determining the centerline of the blood vessel in the enhanced image based on a fast marching algorithm.

* * * * *